(12) United States Patent
Melsky et al.

(10) Patent No.: US 11,832,878 B2
(45) Date of Patent: Dec. 5, 2023

(54) ABLATION SYSTEM WITH AUTOMATED ABLATION ENERGY ELEMENT

(71) Applicant: CardioFocus, Inc., Marlborough, MA (US)

(72) Inventors: Gerald Melsky, Lexington, MA (US); Brian Estabrook, Foxboro, MA (US)

(73) Assignee: CARDIOFOCUS, INC., Marlborough, MA (US)

( * ) Notice: Subject to any disclaimer, the term of this patent is extended or adjusted under 35 U.S.C. 154(b) by 354 days.

(21) Appl. No.: 16/910,416

(22) Filed: Jun. 24, 2020

(65) Prior Publication Data

US 2020/0315704 A1    Oct. 8, 2020

Related U.S. Application Data

(62) Division of application No. 15/399,304, filed on Jan. 5, 2017, now Pat. No. 11,344,365.

(60) Provisional application No. 62/275,017, filed on Jan. 5, 2016.

(51) Int. Cl.
*A61B 34/00* (2016.01)
*A61B 18/00* (2006.01)
*A61B 18/14* (2006.01)
*A61B 18/08* (2006.01)
*A61B 18/24* (2006.01)

(52) U.S. Cl.
CPC ........ *A61B 18/1492* (2013.01); *A61B 18/082* (2013.01); *A61B 34/25* (2016.02); *A61B 18/24* (2013.01); *A61B 2018/0022* (2013.01); *A61B 2018/00351* (2013.01); *A61B 2018/00357* (2013.01); *A61B 2018/00577* (2013.01)

(58) Field of Classification Search
None
See application file for complete search history.

(56) References Cited

U.S. PATENT DOCUMENTS

| 4,445,892 A | 5/1984 | Hussein et al. |
| 4,718,417 A | 1/1988 | Kittrell et al. |
| 4,862,886 A | 9/1989 | Clarke et al. |

(Continued)

FOREIGN PATENT DOCUMENTS

| AU | 741167 | 11/2001 |
| EP | 0292695 | 11/1988 |

(Continued)

OTHER PUBLICATIONS

Tanaka, Kazushi et al., "A New Radiofrequency Thermal Balloon Catheter for Pulmonary Vein Isolation", Journal of the American College of Cardiology, vol. 38, No. 7, Aug. 28, 2001.

*Primary Examiner* — Catherine M Voorhees
*Assistant Examiner* — Elizabeth K So
(74) *Attorney, Agent, or Firm* — Leason Ellis LLP

(57) ABSTRACT

The present disclosure relates to ablation instruments and methods of use thereof, in particular to ablation catheters and methods for an automated sweeping ablation element. The automated sweeping ablation element is configured to provide ablative energy to an initial ablation site and move a predetermined number of degrees to one or both sides of the site in an arcuate path using a sweeping motion while still providing the ablative energy. The sweeping movement of the ablation element can be automated via input parameters entered by a user via a graphical user interface or other device (controller).

6 Claims, 14 Drawing Sheets

(56) References Cited

U.S. PATENT DOCUMENTS

| | | |
|---|---|---|
| 4,878,725 A | 11/1989 | Hessel et al. |
| 4,913,142 A | 4/1990 | Kittrell et al. |
| 4,961,738 A | 10/1990 | Mackin |
| 5,030,201 A | 7/1991 | Palestrant |
| 5,053,033 A | 10/1991 | Clarke |
| 5,078,681 A | 1/1992 | Kawashima et al. |
| 5,109,859 A | 5/1992 | Jenkins |
| 5,125,925 A | 6/1992 | Lundahl |
| 5,133,709 A | 7/1992 | Prince |
| 5,188,632 A | 2/1993 | Goldenberg |
| 5,188,634 A | 2/1993 | Hussein et al. |
| RE34,544 E | 2/1994 | Spears |
| 5,318,024 A | 6/1994 | Kittrell et al. |
| 5,395,362 A | 3/1995 | Sacharoff et al. |
| 5,409,483 A | 4/1995 | Campbell et al. |
| 5,417,653 A | 5/1995 | Sahota et al. |
| 5,496,305 A | 3/1996 | Kittrell et al. |
| 5,575,766 A | 11/1996 | Swartz et al. |
| 5,632,767 A | 5/1997 | Sinofsky |
| 5,643,253 A | 7/1997 | Baxter et al. |
| 5,680,860 A | 10/1997 | Imran |
| 5,693,043 A | 12/1997 | Kittrell et al. |
| 5,722,401 A | 3/1998 | Pietroski et al. |
| 5,725,522 A | 3/1998 | Sinofsky |
| 5,769,843 A | 6/1998 | Abela et al. |
| 5,772,590 A | 6/1998 | Webster, Jr. |
| 5,773,835 A | 6/1998 | Sinofsky |
| 5,782,239 A | 7/1998 | Webster, Jr. |
| 5,782,899 A | 7/1998 | Imran |
| 5,800,482 A | 9/1998 | Pomeranz et al. |
| 5,807,395 A | 9/1998 | Mulier et al. |
| 5,833,682 A | 11/1998 | Amplatz et al. |
| 5,843,073 A | 12/1998 | Sinofsky |
| 5,846,223 A | 12/1998 | Swartz et al. |
| 5,860,974 A | 1/1999 | Abele |
| 5,891,133 A | 4/1999 | Murphy-Chutorian |
| 5,891,134 A | 4/1999 | Goble et al. |
| 5,904,651 A | 5/1999 | Swanson et al. |
| 5,908,415 A | 6/1999 | Sinofsky |
| 5,908,448 A | 6/1999 | Roberts et al. |
| 5,967,984 A | 10/1999 | Chu et al. |
| 6,004,269 A | 12/1999 | Crowley et al. |
| 6,012,457 A | 1/2000 | Lesh |
| 6,024,740 A | 2/2000 | Lesh et al. |
| 6,056,744 A | 5/2000 | Edwards |
| 6,071,281 A | 6/2000 | Burnside et al. |
| 6,086,581 A | 7/2000 | Reynolds et al. |
| 6,102,905 A | 8/2000 | Baxter et al. |
| 6,117,101 A | 9/2000 | Diederich et al. |
| 6,120,496 A | 9/2000 | Whayne et al. |
| 6,159,203 A | 12/2000 | Sinofsky |
| 6,164,283 A | 12/2000 | Lesh |
| 6,179,835 B1 | 1/2001 | Panescu et al. |
| 6,245,064 B1 | 6/2001 | Lesh et al. |
| 6,251,109 B1 | 6/2001 | Hassett et al. |
| 6,254,599 B1 | 7/2001 | Lesh et al. |
| 6,270,492 B1 | 8/2001 | Sinofsky |
| 6,305,378 B1 | 10/2001 | Lesh |
| 6,314,962 B1 | 11/2001 | Vaska et al. |
| 6,325,797 B1 | 12/2001 | Stewart et al. |
| 6,375,654 B1 | 4/2002 | Mcintyre |
| 6,383,151 B1 | 5/2002 | Diederich et al. |
| 6,416,511 B1 | 7/2002 | Lesh et al. |
| 6,423,055 B1 | 7/2002 | Farr et al. |
| 6,423,058 B1 | 7/2002 | Edwards et al. |
| 6,471,697 B1 | 10/2002 | Lesh |
| 6,500,174 B1 | 12/2002 | Maguire et al. |
| 6,502,576 B1 | 1/2003 | Lesh |
| 6,514,249 B1 | 2/2003 | Maguire et al. |
| 6,547,780 B1 | 4/2003 | Sinofsky |
| 6,558,375 B1 | 5/2003 | Sinofsky et al. |
| 6,572,609 B1 | 6/2003 | Farr et al. |
| 6,579,285 B2 | 6/2003 | Sinofsky |
| 6,605,055 B1 | 8/2003 | Sinofsky |
| 6,605,084 B2 | 8/2003 | Acker et al. |
| 6,626,900 B1 | 9/2003 | Sinofsky et al. |
| 6,635,054 B2 | 10/2003 | Fjield et al. |
| 6,652,515 B1 | 11/2003 | Maguire et al. |
| 6,676,656 B2 | 1/2004 | Sinofsky |
| 6,771,996 B2 | 8/2004 | Bowe et al. |
| 6,796,972 B1 | 9/2004 | Sinofsky et al. |
| 6,932,809 B2 | 8/2005 | Sinofsky |
| 6,942,657 B2 | 9/2005 | Sinofsky et al. |
| 6,953,457 B2 | 10/2005 | Farr et al. |
| 6,964,660 B2 | 11/2005 | Maguire et al. |
| 6,971,394 B2 | 12/2005 | Sliwa, Jr. et al. |
| 6,997,924 B2 | 2/2006 | Schwartz et al. |
| 7,137,395 B2 | 11/2006 | Fried et al. |
| 7,207,984 B2 | 4/2007 | Farr et al. |
| 7,357,796 B2 | 4/2008 | Farr et al. |
| 7,540,846 B2 | 6/2009 | Harhen et al. |
| 7,655,005 B2 | 2/2010 | Bhola |
| 7,935,108 B2 | 5/2011 | Baxter et al. |
| 7,952,718 B2 | 5/2011 | Li et al. |
| 8,025,661 B2 | 9/2011 | Arnold et al. |
| 8,114,073 B2 | 2/2012 | Whayne et al. |
| 8,152,795 B2 | 4/2012 | Farr et al. |
| 8,231,613 B2 | 7/2012 | Baxter et al. |
| 8,241,272 B2 | 8/2012 | Arnold et al. |
| 8,267,932 B2 | 9/2012 | Baxter et al. |
| 8,277,444 B2 | 10/2012 | Arnold et al. |
| 8,366,705 B2 | 2/2013 | Arnold et al. |
| 8,444,639 B2 | 5/2013 | Arnold et al. |
| 8,540,704 B2 | 9/2013 | Melsky et al. |
| 8,617,150 B2 | 12/2013 | Tsoref et al. |
| 8,696,653 B2 | 4/2014 | Melsky et al. |
| 8,702,688 B2 | 4/2014 | Melsky |
| 8,805,466 B2 | 8/2014 | Salahich et al. |
| 8,900,219 B2 | 12/2014 | Sinofsky et al. |
| 9,033,961 B2 | 5/2015 | Melsky et al. |
| 9,421,066 B2 | 8/2016 | Melsky et al. |
| 9,492,231 B2 | 11/2016 | Cisel et al. |
| 9,622,706 B2 | 4/2017 | Dick et al. |
| 10,105,184 B2 | 10/2018 | Beck et al. |
| 10,349,966 B2 | 7/2019 | Thapliyal et al. |
| 10,517,669 B2 | 12/2019 | Peled et al. |
| 2002/0019627 A1 | 2/2002 | Maguire et al. |
| 2002/0029062 A1 | 3/2002 | Satake |
| 2002/0052621 A1 | 5/2002 | Fried et al. |
| 2002/0065512 A1 | 5/2002 | Fjield et al. |
| 2002/0091383 A1 | 7/2002 | Hooven |
| 2002/0107511 A1 | 8/2002 | Collins et al. |
| 2002/0115995 A1 | 8/2002 | Lesh et al. |
| 2003/0050632 A1 | 3/2003 | Fjield et al. |
| 2003/0065307 A1 | 4/2003 | Lesh |
| 2003/0069620 A1 | 4/2003 | Li |
| 2003/0109778 A1 | 6/2003 | Rashidi |
| 2003/0111085 A1 | 6/2003 | Lesh |
| 2003/0120270 A1 | 6/2003 | Acker |
| 2004/0006333 A1 | 1/2004 | Arnold et al. |
| 2004/0059397 A1 | 3/2004 | Sinofsky et al. |
| 2005/0038419 A9 | 2/2005 | Arnold et al. |
| 2005/0065504 A1 | 3/2005 | Melsky et al. |
| 2005/0222558 A1 | 10/2005 | Baxter et al. |
| 2005/0234436 A1 | 10/2005 | Baxter et al. |
| 2005/0234437 A1 | 10/2005 | Baxter et al. |
| 2006/0122584 A1 | 6/2006 | Bommannan et al. |
| 2006/0253113 A1 | 11/2006 | Arnold et al. |
| 2007/0078451 A1 | 4/2007 | Arnold et al. |
| 2008/0015569 A1 | 1/2008 | Saadat et al. |
| 2008/0097476 A1 | 4/2008 | Peh et al. |
| 2008/0300588 A1 | 12/2008 | Groth et al. |
| 2009/0131931 A1 | 5/2009 | Lee et al. |
| 2009/0137996 A1* | 5/2009 | DeBenedictis ...... A61B 18/203 606/9 |
| 2009/0171271 A1* | 7/2009 | Webster ............. A61B 17/3421 604/95.01 |
| 2009/0221996 A1 | 9/2009 | Lesh et al. |
| 2009/0221997 A1 | 9/2009 | Arnold et al. |
| 2009/0275934 A1 | 11/2009 | Baxter et al. |
| 2009/0299354 A1 | 12/2009 | Melsky et al. |
| 2009/0326320 A1 | 12/2009 | Sinofsky et al. |
| 2010/0042084 A1 | 2/2010 | Nogawa |
| 2010/0168624 A1 | 7/2010 | Sliwa |

(56) References Cited

U.S. PATENT DOCUMENTS

| | | |
|---|---|---|
| 2010/0198065 A1 | 8/2010 | Thapliyal et al. |
| 2010/0317962 A1 | 12/2010 | Jenkins |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0245822 A1 | 10/2011 | Baxter et al. |
| 2011/0245828 A1 | 10/2011 | Baxter et al. |
| 2011/0301508 A1 | 12/2011 | Sethuraman et al. |
| 2012/0157981 A1 | 6/2012 | Evans et al. |
| 2012/0289950 A1 | 11/2012 | Neuberger |
| 2013/0012923 A1 | 1/2013 | Baxter et al. |
| 2013/0018303 A1* | 1/2013 | Webster ............ A61M 25/0127 604/95.01 |
| 2013/0035537 A1 | 2/2013 | Wallace et al. |
| 2013/0289358 A1 | 10/2013 | Melsky et al. |
| 2013/0345541 A1 | 12/2013 | Nau, Jr. |
| 2014/0005706 A1 | 1/2014 | Gelfand et al. |
| 2014/0031802 A1 | 1/2014 | Melsky et al. |
| 2014/0081254 A1 | 3/2014 | Rudie |
| 2014/0081302 A1 | 3/2014 | Thapliyal et al. |
| 2014/0276398 A1 | 9/2014 | Goodman et al. |
| 2015/0182275 A1 | 7/2015 | Tsoref et al. |
| 2015/0182284 A1 | 7/2015 | Peled et al. |
| 2015/0257830 A1 | 9/2015 | Tyc et al. |
| 2015/0305604 A1 | 10/2015 | Melsky |
| 2016/0157954 A1 | 6/2016 | Sagon et al. |
| 2017/0189109 A1 | 7/2017 | Melsky et al. |
| 2018/0193078 A1 | 7/2018 | Rajagopalan et al. |
| 2018/0271581 A1 | 9/2018 | Ouyang et al. |

FOREIGN PATENT DOCUMENTS

| | | |
|---|---|---|
| EP | 0439629 | 8/1991 |
| EP | 1 009 303 | 6/2000 |
| EP | 1207788 | 5/2002 |
| EP | 1289439 | 3/2003 |
| EP | 1331893 | 12/2004 |
| EP | 1758518 A2 | 3/2007 |
| GB | 2453601 B | 4/2009 |
| JP | 2001-504363 | 4/2001 |
| JP | 2005237827 A | 9/2005 |
| JP | 2006-516465 | 7/2006 |
| JP | 2009543607 | 12/2009 |
| JP | 2016-502892 | 2/2016 |
| WO | WO 9607451 | 3/1996 |
| WO | WO 9640342 | 12/1996 |
| WO | WO 9737714 | 10/1997 |
| WO | WO 00/67656 | 11/2000 |
| WO | WO 00/67832 | 11/2000 |
| WO | WO 01/03599 A2 | 1/2001 |
| WO | WO 01/64123 | 9/2001 |
| WO | WO 03090835 | 11/2003 |
| WO | WO 2004-110258 | 12/2004 |
| WO | WO 2010/120881 | 10/2010 |
| WO | WO 2010/120883 | 10/2010 |
| WO | WO 2011/041629 | 4/2011 |
| WO | WO 2011/041635 | 4/2011 |
| WO | WO 2011/041638 | 4/2011 |
| WO | WO 2011/044248 | 4/2011 |
| WO | WO 2014/109879 | 7/2014 |
| WO | WO 2015/167929 | 11/2015 |
| WO | WO 2016/089900 | 6/2016 |

\* cited by examiner

ABLATION SYSTEM WITH AUTOMATED ABLATION ENERGY ELEMENT

CROSS REFERENCE TO RELATED APPLICATION

The present application is a divisional of U.S. patent application Ser. No. 15/399,304, filed Jan. 5, 2017, now U.S. Pat. No. 11,344,365, issued May 31, 2022, which claims priority to U.S. patent application Ser. No. 62/275,017, filed Jan. 5, 2016, all of which are incorporated by reference, as if expressly set forth in their respective entireties herein.

TECHNICAL FIELD

The present disclosure relates to ablation instruments and methods of use thereof, in particular to ablation catheters and methods for performing ablation procedures utilizing an ablation element that can be automated and moves in a sweeping motion and in overlapping increments to provide a customizable scope of coverage of the ablation energy.

BACKGROUND

Cardiac arrhythmias (e.g., fibrillation) are irregularities in the normal beating pattern of the heart and can manifest themselves in either the atria or the ventricles of the heart. For example, atrial fibrillation is a form of arrhythmia characterized by rapid randomized contractions of atrial myocardium, causing an irregular, often rapid ventricular response. The regular pumping function of the atria is replaced by a disorganized, ineffective quivering as a result of chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy, or hypertension.

It is now understood that recurrent atrial fibrillation (paroxysmal and persistent) is triggered by rapidly firing tissue, (called "ectopic foci"), that are principally located in one or more of the four pulmonary veins, which attach to the rear of the left atrium. It has been found that atrial fibrillation may be prevented by electrically isolating the pulmonary veins from the rest of the left atrium.

Various techniques have been employed for pulmonary vein isolation. A common purpose of each of these techniques is to replace cardiac muscle cells with scar tissue, which scar tissue cannot conduct normal electrical activity within the heart.

In one known approach, circumferential ablation of tissue surrounding the junction of the pulmonary veins and the left atrium has been practiced to treat atrial fibrillation. By ablating the heart tissue at this location transmurally and circumferentially, electrical conductivity between the pulmonary veins and the remainder of the left atrium can be blocked as a result of creating this scar or durable barrier, preventing the initiation of the fibrillatory process.

Several types of ablation devices have recently been proposed for creating lesions to treat cardiac arrhythmias. Many of the recently proposed ablation instruments are percutaneous devices that are designed to create individual lesions from within the heart. Such devices are positioned in the heart by catheterization of the patient, e.g., by passing the ablation instrument into the heart via a blood vessel, such as the femoral vein and then gaining transseptal access to the left atrium.

Typically, percutaneous devices are positioned with the assistance of a guide catheter, which is first advanced into the left side of the heart through a hole made in the intraatrial septum. In one increasingly common approach, a guide catheter or similar guide device is advanced through the vasculature and into the left atrium of the heart. A catheter instrument with an expandable element is then advanced through the guide catheter and into each one of the ostia of pulmonary veins where the expandable element (e.g., a balloon) is inflated. The balloon includes a moveable ablation element, e.g., an energy emitting device, such as a laser, disposed in the inner surface of the balloon, which allows the physician to sequentially position and control the application of energy in the area of the junction between the vein ostium and the left atrium to create a durable barrier which is the objective of the ablation procedure.

A number of ablation systems operate by emitting ablation energy, such as a laser beam, that has a circumferential shape or has a shape that is less than a complete circumference (i.e., arc shaped). While these systems are effective, in the case of devices which emit arc-shaped ablation energy, the user may have to incrementally move the ablation element using a significant number of steps to complete the lesion. This process can be time consuming since the ablation element may be configured to only emit a small arc of energy (e.g., subtending at an angle from about 5 to 30 degrees relative to the energy emitter in one embodiment).

Thus, there remains a need in the art for systems and methods configured to accurately and immediately confirm whether the pulmonary vein isolation procedure was successful, thereby allowing the user (electrophysiologist, more specifically an electrophysiologist or interventional cardiologist) to take corrective action in real time to ensure a complete circumferential barrier has been durably formed. There also remains a need in the art for systems and methods configured to more efficiently complete the lesion.

SUMMARY

The present invention relates to ablation equipment, such as an ablation catheter, configured to have an ablation element that can undergo a programmed (user inputted), controlled sweeping action. The ablation element is configured to provide ablative energy to an initial ablation site and then move a predetermined number of degrees to one or both sides of the initial ablation site in an arcuate path using a sweeping motion while still providing the ablative energy. The sweeping motion of the ablation element results in a larger arcuate shaped ablation segment being formed even though the actual ablation element is configured to emit a smaller sized arcuate shaped ablation segment. The sweeping action thus allows the ablation element to complete a continuous circumferential lesion by making only a few number of arcuate shaped lesion segments compared to the previous technique of performing one arcuate ablation segment at one time. The movement of the ablation element can be programmed by an operator via a graphical user interface, wherein the operator inputs the desired controlled parameters which are then executed. The input parameters provided by the operator configure the ablation element to make automated lesion segments at the target site to complete a continuous lesion. Using the graphical user interface, the ablation element can be configured to move both rotationally (sweeping action) and axially within the catheter body to position the ablation element at the target site. The input parameters can configure the ablation element to move in a controlled sweeping action over a predetermined number of degrees of travel. The input parameters can also control the power of the ablative energy provided by the ablation element to the target site and also the time. In addition, the elapsed time period for a discrete sweeping action can also be controlled and inputted by the user. The discrete sweeping action during energy delivery could be executed as a single sweep or as multiple sweeps over the targeted tissue.

The ablation equipment of the present application can further include a console having a display, the console being operatively connected to the ablation instrument. Using the console, the operator can input parameters via the graphical user interface for the automated movement of the ablation element. In one aspect, software can be used to automatically calculate the pathway of the ablation element using only select input parameters that have been entered by the operator.

The ablation instrument of the present application can include a motor, such as a servomotor, which is configured to rotate the ablation element in a sweeping motion based on the input parameters. In another aspect, the ablation instrument can include a second motor configured to move the ablation element axially within the catheter. The one or more motors can be coupled with an encoder to provide position and speed feedback to assist in controlling the motion and final position of the ablation element. The one or more motors can be located in a handle of the ablation instrument or in the console of the instrument or located at another location.

These and other aspects, features and benefits of the invention can be further appreciated from the accompanying drawings, which illustrate certain embodiments of the invention together with the detailed description thereof.

BRIEF DESCRIPTION OF THE DRAWINGS

The objects and features of the invention may be understood with reference to the following detailed description of an illustrative embodiment of the present invention taken together in conjunction with the accompanying drawings in which.

DETAILED DESCRIPTION OF CERTAIN EMBODIMENTS OF THE INVENTION

The present invention will now be described more fully with reference to the accompanying drawings, in which illustrated embodiments of the present invention are shown. The present invention is not limited in any way to any of the illustrated embodiments.

As described in detail below, the present invention relates to ablation equipment/ablation system, such as an ablation catheter, that is configured to have a visualization feature (functionality) that allows the user to determine, in real-time, whether a complete lesion has been formed by monitoring the state of the electrical activity at the target site and more specifically, by monitoring a visual change in a pool of blood that is located distal to the target site. In one embodiment, the visual change in the pool of blood (e.g., blood in the pulmonary vein) is represented by a change in the visible pattern of perturbation of the blood pool since at an initial pre-procedure point (i.e., a baseline), vigorous activation is visible in the blood pool (i.e., a high degree of perturbation of the blood pool) and as the ablation procedure progresses, incremental lessening in the vigorous nature of blood pool movement becomes visible (due to the progressive formation of a circumferential lesion and a concomitant reduction in electrical activity distal to the target site).

A display, such as a computer monitor, presents images in real time that allow the user to determine whether the formed lesion has had the desired effect on the electrical activity at the target site (i.e., electrical isolation). In other words, the system of the present invention is configured to provide the user with real-time visualization information that allows the user to determine whether a complete lesion has been formed at the target site. In addition, a visualization module can be provided along with software that allows a comparison between two or more images of the target site.

Since the sufficiency of the lesion is immediately and readily determinable, the user (electrophysiologist) can detect whether a complete lesion has been formed and in the event that there are any deficiencies in the lesion, such as gaps or breaks in the lesion, the user can take immediate corrective measures.

Figure 1:
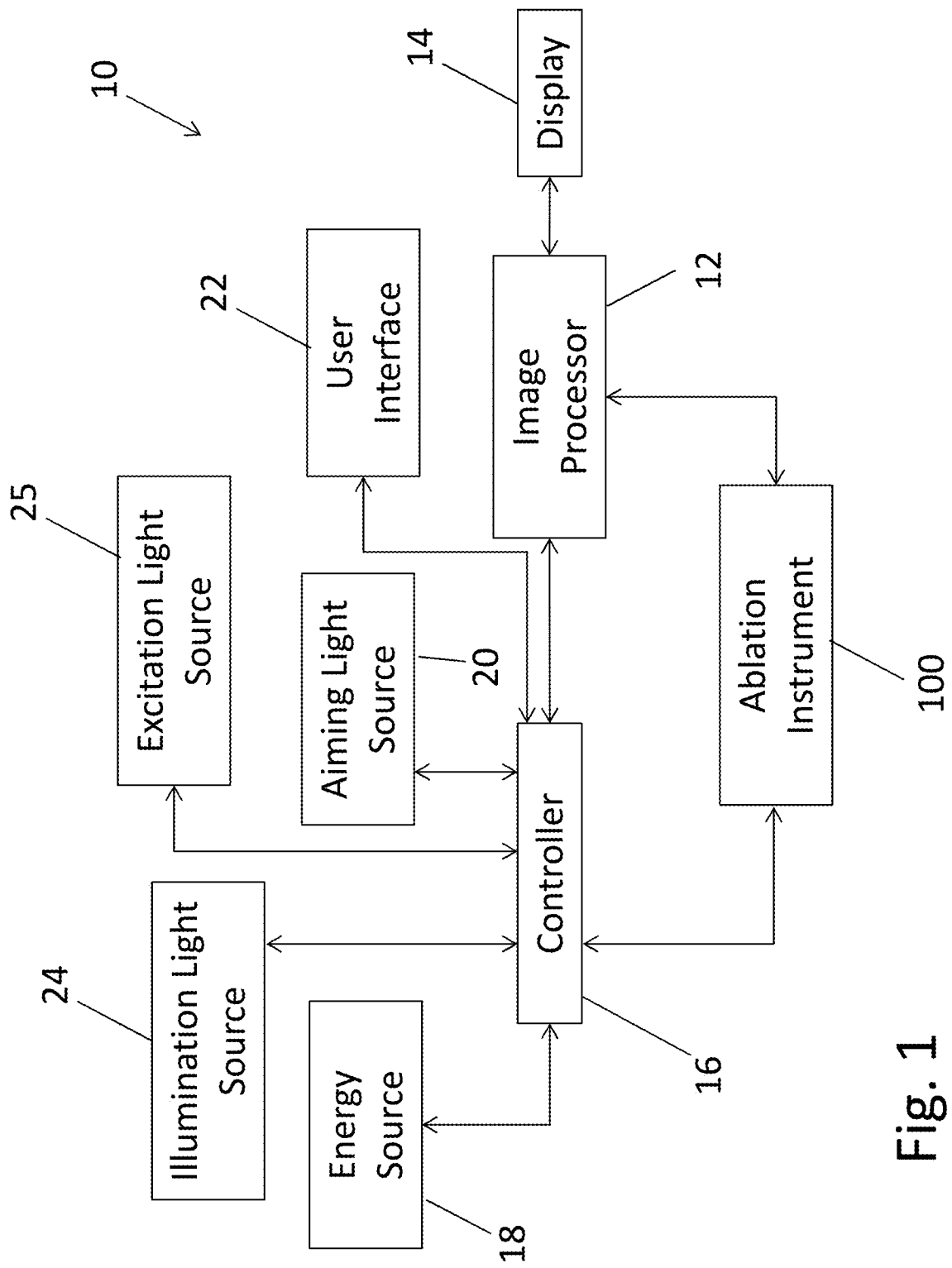
FIG. 1 is a block diagram depicting the components of an endoscope-guided cardiac ablation system according to the invention.

FIG. 1 is a schematic block diagram illustrating an ablation/endoscopic system in accordance with the invention, designated generally by reference numeral 10. Ablation system 10 preferably includes a treatment ablation instrument 100 preferably including an endoscope and ablation device (energy emitter) as discussed below. The treatment ablation instrument 100 can be any number of different ablation instruments that are commercially available including those disclosed by Applicant in previous U.S. patents and patent applications (e.g., U.S. patent application publication Nos. 2009/0326320 and 2011/0082451, each of which is hereby incorporated by reference in its entirety). In general, the ablation instrument 100 is of a type that emits ablation energy sufficient to cause formation of an ablation at a tissue target site.

The ablator system 10 further preferably includes an aiming light source 20 and an illumination light source 24. A processor 12 designed to accept input and output data from the connected instruments, a display 14, and a controller 16 and process that data into visual information.

As will also be appreciated from the below discussion, an endoscope is preferably provided in ablation instrument 100 and has the capability of capturing both live images and recording still images. An illumination light 24 is used to provide operating light to the treatment site. The illumination light is of a frequency that allows the user to differentiate between different tissues present at the operating site. An aiming light source 20 is used to visualize the location where energy will be delivered by the ablation instrument 100 to tissue. It is envisioned that the aiming light 20 will be of a wavelength that can be recorded by an image capture device and visible on a display.

Composite Imaging System

The processor 12 is preferably designed to process live visual data as well as data from the ablation instrument controllers and display. The processor 12 is configured execute a series of software and/or hardware modules configured to interpret, manipulate and record visual information received from the treatment site. The processor 12 is further configured to manipulate and provide illustrative and graphical overlays and composite or hybrid visual data to the display device.

As seen in FIG. 1, the system 10 further includes the controller 16, an energy source 18, the aiming light source 20 and a user interface 22. Controller 16 is preferably configured to control the output of the energy source 18 and the illumination and excitation sources 24 and 25 of an energy transmitter, as well as being configured to determine the distance and movement of an energy transmitter relative to tissue at an ablation treatment site (as discussed further below). As will also be appreciated from the below discussion, an endoscope is preferably supported by the ablation instrument 100 and captures images that can be processed by the processor 12 to determine whether sufficient ablative energy deliveries have been directed to a specific area of a treatment site. Data obtained from the endoscope includes real-time video or still images of the treatment site as seen from the ablation instrument. As discussed herein, these images/videos can be stored in memory for later use.

The aiming light source 20 is used to visualize the treatment site location 120 where energy will be delivered by the ablation instrument 100 to tissue 130. Preferably, the aiming light source 20 outputs light in a visible region of the electromagnetic spectrum. If a suitable ablation path is seen by the user, the controller 16 transmits radiant energy, via energy source 18, from the ablation instrument 100 to a target tissue site 152 (FIG. 8) to effect ablation by lesions. It is to be appreciated that the term "radiant energy" as used herein is intended to encompass energy sources that do not rely primarily on conductive or convective heat transfer. Such sources include, but are not limited to, acoustic, laser and electromagnetic radiation sources and, more specifically, include microwave, x-ray, gamma-ray, ultrasonic and radiant light sources. Additionally, the term "light" as used herein is intended to encompass electromagnetic radiation including, but not limited to, visible light, infrared and ultraviolet radiation.

The illumination light source 24 is a light source used to provide proper illumination to the treatment site. The illuminate is configured so that natural biological tones and hues can be easily identifiable by an operator.

The controller 16 can provide the user with the ability to control the function of the aiming light source, the user input devices, and the ablation instrument. The controller 16 serves as the primary control interface for the ablation system. Through the controller 16, the user can turn on and off both the aiming and illumination lights 20, 24. Furthermore the controller 16 possesses the ability to change the illumination and aiming light intensity. The ability to switch user interfaces or display devices is also envisioned. Additionally, the controller 16 gives access to the ablation instrument 100, including control over the intensity of the discharge, duration and location of ablative energy discharges. The controller 16 can further provide a safety shutoff to the system in the event that a clear transmission pathway between the radiant energy source and the target tissue is lost during energy delivery (e.g., see commonly owned U.S. patent application Ser. No. 12/896,010, filed Oct. 1, 2010, which is hereby incorporated by reference in its entirety).

The controller can be a separate microprocessor based control interface hardware or it can be a portion of a configured as a module operating through a processor based computer system configured to accept and control inputs from various physical devices.

Figure 3:
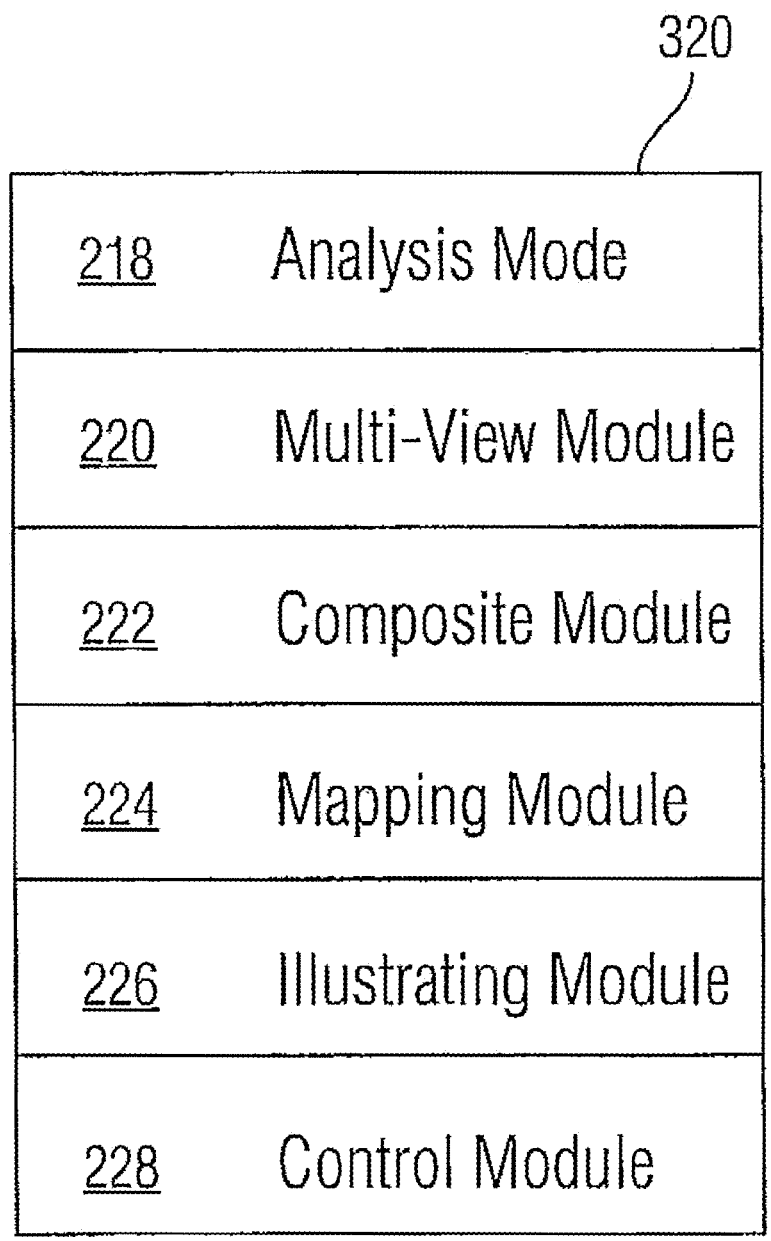
FIG. 3 is a block diagram of the processor modules used in the cardiac ablation instrument.

As shown in FIG. 3, a set of modules cooperate with one another to provide the information presented through the interface 22 of the system of FIG. 1. Thus, for example, there can be an analysis module 218, a multiple view module 220, a composite module 222, a mapping module 224, an illustrating module 226, and a control interface module 228. Each of these modules can comprise hardware, code executing in a processor, or both, that configures a machine, such as a workstation, to implement the functionality described herein.

With further reference to FIG. 3, the analysis module 218 includes instructions for analyzing a lesion and determining if it is sufficient for the desired treatment. The analysis module 218 can be configured to inspect the image data captured by the image capture device (e.g., an endoscope) and determine whether a lesion of sufficient dimensions and quality has been formed based in part on an analysis of pre-procedure motion (electrical activity) at the target site and post-procedure motion (electrical activity). The analysis module 218 can be implemented as discrete sub-modules to provide functions such as receiving data on the duration and intensity of an ablative emission. An additional submodule is capable of evaluating the duration of the energy emission and comparing it to a look up table of sufficient duration and intensity values suitable to form a proper lesion.

The multiple view module 220 includes instructions for configuring the processor 12 to provide multiple images to the display. The multiple view module configures the display to depict at least two image depiction areas. In a first image depiction area, the live video stream of the treatment site is displayed to the user. In a second image depiction area, a still image, highlighting the last target of ablative energy is depicted or depicting other information such as a baseline image as described below.

The composite module 222 includes instructions for combining a series of still images and producing a composite image that depicts the target location of the ablative emission in each still image. The compositing module 222 can be implemented as discrete sub-modules to provide functions such as altering the transparency of each still image layer of the composite image so that a time based map of ablation locations can be produced. Another function implemented by the submodules is construction of a video or slideshow from a sequence of still images. It will be understood that the composite module 222 is optional.

The mapping module 224 includes instructions for overlaying proposed treatment paths on the live image. The mapping module can be configured to show colored markers indicating acceptable levels of ablative energy depositing. For example the mapping module is capable of generating a colored visual marker and superposing it over the live image to indicate areas that have yet to receive levels of ablative energy necessary for treatment. Conversely, the mapping module 224 is also capable of simultaneously generating a red colored (or other color) visual marker and superimposing it over the live image to indicate areas that have received sufficient quantities of ablative energy suitable lesions. The mapping module 224 can be implemented as discrete sub-modules to provide functions such as receiving data on the duration and intensity of an ablative emission and correlating that specific instance to a specific stored image.

In accordance with one aspect of the present invention, the mapping module 224 can be configured to superimpose a live image of the distal blood pool over the pre-procedure image of the distal blood pool to allow a visual comparison therebetween (which is indicative of the sufficiency (degree of completion) of the ablation.

It will also be understood that the mapping module 224 is optional.

Figure 2:
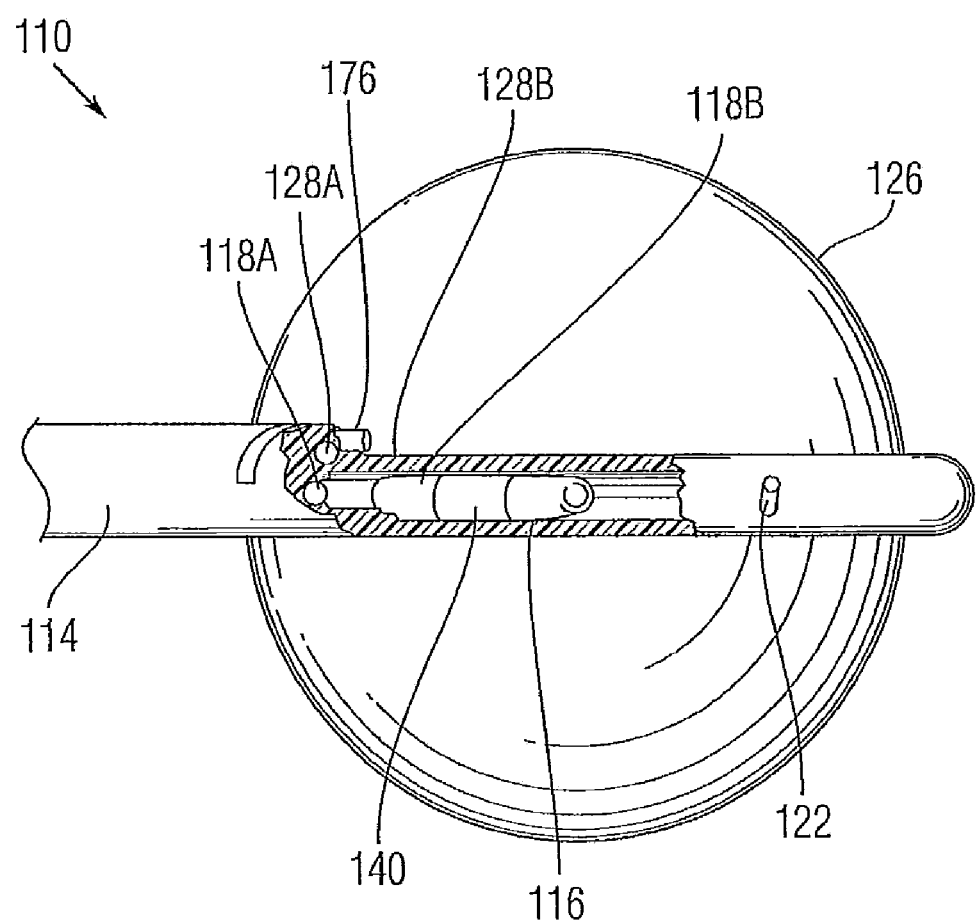
FIG. 2 is a schematic view of the of the cardiac ablation instrument of the cardiac ablation system of FIG. 1.
Figure 8:
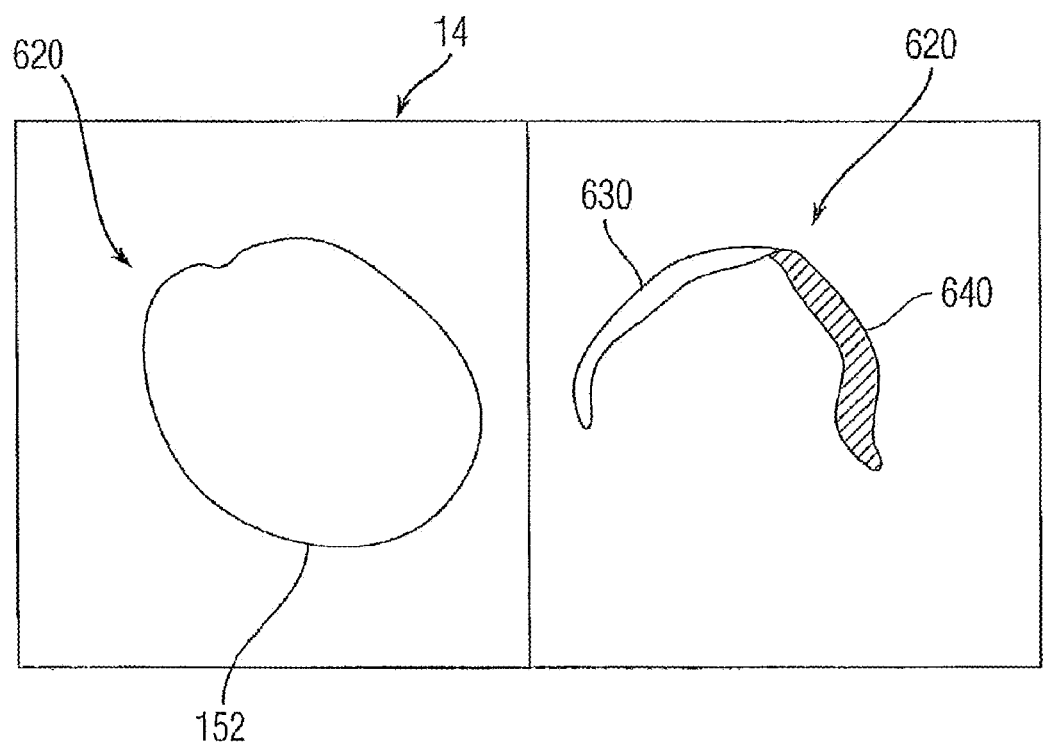
FIG. 8 is a screen shot of the display of FIG. 1 depicting visual warning signals indicative of insufficient lesions.

The illustrating module 226 includes instructions for providing an image to the display, wherein the image is an illustration or graphical representation of the treatment site. The illustrating module 226 is configured to allow annotation of the illustrated image as well as comparison between the live image and the illustrated image. For example, and as shown in FIG. 8, display 14 provides a first screen portion 610 depicting the actual treatment site 152 as viewed from endoscope 176 (FIG. 2). Display 14 can also illustrate a second screen portion 620 illustrating a graphical depiction of the treatment site 152 indicating the actual path of the energy transmitter 140 on the tissue at the treatment site wherein the path consists of a trace indicating the sufficiency of the formed lesions in which a solid trace 630 indicates sufficient lesions and a hashed trace 640 indicates insufficient lesions. The illustrating module 226 is also optional.

In one embodiment, the system can be configured so as to at least contain the analysis module 218, the multiple view module 220, the illustrating module 226, and the control interface module 228.

The control module 220 includes instruction for orientating and accessing the functions of each of the other modules, as well as communicating with the controller and inputting information or manipulating the parameters of the data being displayed during operation. The manipulation and controlling functions can be implemented as discrete sub-modules with instructions for selecting operation modes, control interfaces, display orientation, recording modes, storage device location and data entry.

Figure 4:
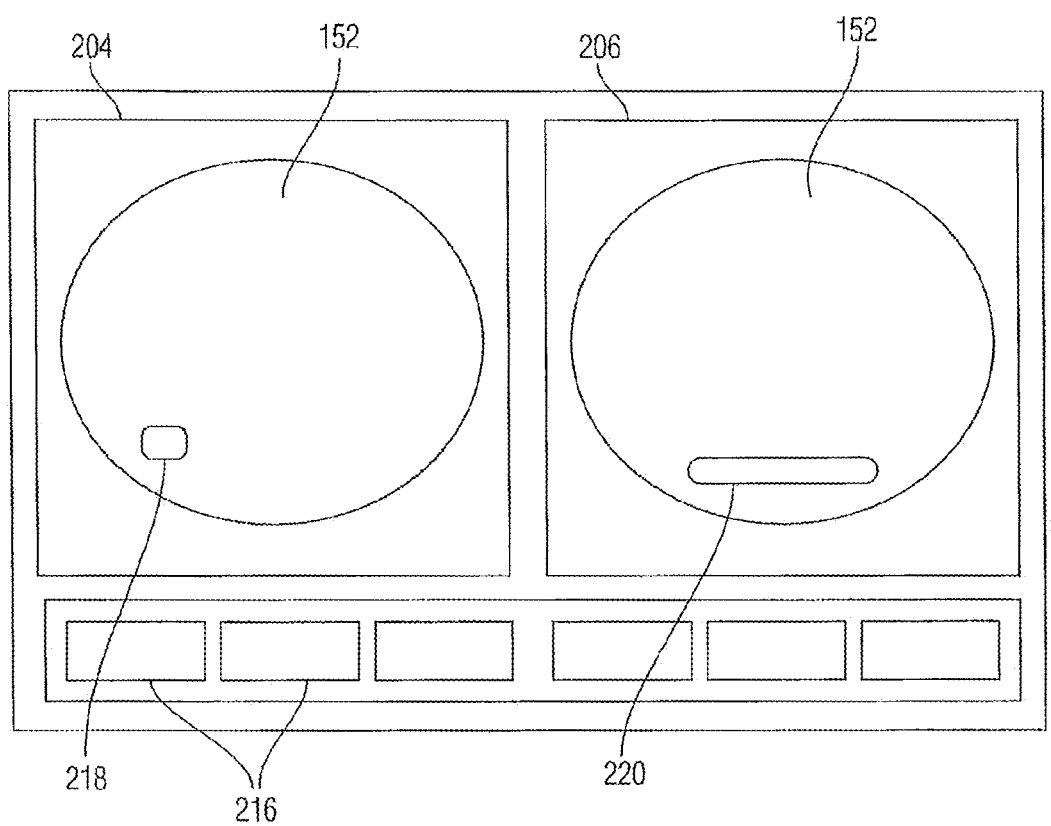
FIG. 4 illustrates a user interface in the form of a split-screen arrangement for displaying information.

The user refers to the live video feed from the image capture device to determine where to direct a radiant energy transmission. Upon first use of the device, a live video image and a still image of the treatment site are depicted on the display. As seen in FIG. 4, the processor 12 outputs to the display 14 at least two separately defined image depiction areas 204, 206. One image depiction area 204 is reserved for displaying live video transmitted from the treatment site 152. At least one other image depiction area 206 is used to depict an image or a composite image comprised of several still images representing specific moments in time during the treatment (an intracardiac procedure).

The live video shown to the user will allow the user to see the reflection of the aiming light 218 and hence direct ablative energy. It is envisioned that the first still image 210 depicted will be a still image captured at a point in time prior to the initiation of the first radiant energy emission. For instance, at a point in time prior to the emission of radiant energy, the image capture device records an image 210 of the treatment site 152 that depicts the treatment site 152 without the aiming light. By taking a still image 210 of the site, the user can record a baseline image of the treatment site before any treatment has been commenced. Furthermore, through the functions of the illustrative module, an illustration of the untouched 152 can be generated. During emission of radiant energy a still image 210 is taken of the treatment site 152. The characteristics of the ablative event (e.g. information regarding the duration and intensity of the radiance of the energy emission) are stored and associated with the image depicting that specific emission. In addition, the reflection of the aiming light will be visible in the still image, providing a location indicator as to where the energy was directed. A series of these still images can be combined by using the composite module. By modifying the opacity of each image, the reflected light of the aiming light for each ablative event will be visible in the composite image. In this way, a complete record 220 of where energy was directed will become available. Furthermore, because the composite image is composed a series of individual images representing a specific period of time during the procedure, a time based map of the entire operation can also be produced in real time or for subsequent review.

Also visible in FIG. 4 are control interfaces 216 for accessing the control module 228. The control interfaces allow the user to select image style and opacity as well and initiating the functions of the other modules. Furthermore the functions of the controller 16 are also controllable from the control interface 228.

It is to be appreciated the invention is not to be understood to be limited to the two image depiction areas discussed above with reference to FIG. 3 or 4, but rather may encompass any number of image depiction areas in which the images and representations of the treatment site 152 can be reviewed. With reference to FIG. 8 the images shown by the display 14 can be manipulated by the modules to illustrate the presence of sufficient or insufficient lesion formation. For instance, the display 14 may illustrate the image of the treatment site 152 viewed from the endoscope 176 FIG. 2) wherein varying shades of grey and white depict tissue and lesions and in the event insufficient lesions are determined to be formed, or a red marker can be superimposed on the image of the treatment site 152 at the location where the insufficient lesion was determined. Coincidently, an audio signal may also be emitted from ablation system 10 causing further warning to the user.

Therefore, if the user is not satisfied with the quality of the lesion produced, or the modules indicate that a sufficient lesion was not produced, the user can promptly redo the treatment of a specific tissue location (spot treatment). Conversely, if the modules indicate that a sufficient lesion was formed, the user can confidently move on to a new tissue location to continue the treatment thus saving time and effort by avoiding the need to more closely examine the tissue location that was just treated. Hence, once the entire treatment is performed, the modules of the system permit the electrophysiologist to view all treatment segments forming the entire ablation arc to see if a continuous, uninterrupted ablation has been formed (or see if the ablation has the intended, desired shape). If there are visible gaps or other imperfections with the formed ablation, the electrophysiologist can move the energy transmitter (ablation element) 140 to the proper location for retreatment of these areas until the desired ablation is formed. The process can then be repeated to determine and confirm that the gap was eliminated.

As a result, the mapping, analyzing and illustrating functions performed by the ablation system of the present invention overcome the disadvantages associated with prior ablation procedures and results in increased ablation success rates due to a more optimal and more accurate viewing and quality determination of the spot lesions created to form the continuous ablation at the tissue location for the treatment site 152.

Figures 5, 6:
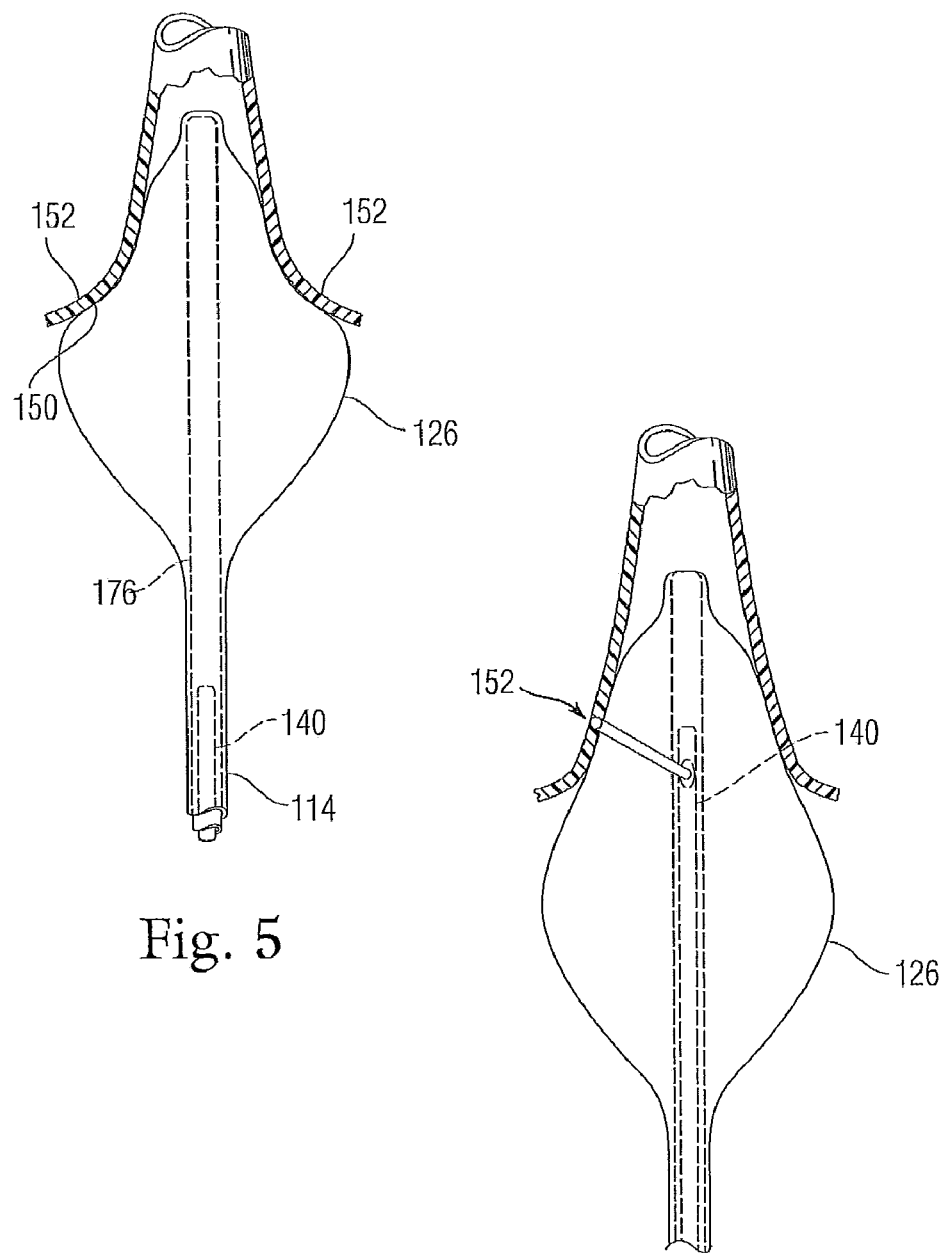
FIG. 5 is a schematic view of the cardiac ablation instrument of FIG. 2 shown in a treatment position within the ostium for treatment of the pulmonary vein.
FIG. 6 is a schematic view of the cardiac ablation instrument of FIG. 2 with its compliant balloon inflated and its ablation element deployed at one of a plurality of locations.

With reference now to FIGS. 2 and 5, a description of ablation instrument 100 is provided. FIG. 5 provides a schematic, cross-sectional view of an ablation instrument 100, including an elongated body 114, a central lumen tubing 116 and a compliant balloon 126 inflatable via one or more ports 122 in the central tubing 116. The central tubing 116 can also house an energy emitter 140 that is capable of both axial movement and rotation within a lumen formed in the elongate body 114. Additionally formed in the elongated body 114 (also referred to herein as the catheter body) there can be a plurality of additional lumens, through which certain devices or instruments can be passed. For example, the catheter body 114 also provides lumens 118A and 118B for extraction (or circulation) of an inflation fluid, an endoscope 176 and illumination and excitation fibers 128A and 128B.

It should be understood that the embodiments illustrated in the drawings are only a few of the cardiac ablation instruments that can be utilized in accordance with the present invention. Further descriptions of other embodiments can be found, for example, in commonly owned, U.S. patent application Ser. No. 10/357,156, filed Feb. 3, 2003, U.S. patent application Ser. No. 09/924,393, filed Aug. 7, 2001—each of which is expressly incorporated by reference.

With reference now to FIGS. 5-6, the ablation instrument 100 is preferably designed such that upon disposition within the heart (e.g., proximal to a pulmonary vein), the balloon 126 can be inflated such that a shoulder portion 150 of the balloon 126 will be urged into close proximity with a target region 152 of cardiac tissue. As shown in FIG. 4, the energy emitter (or "lesion generator") 140 can be positioned to deliver ablative energy to the target region 152 to form a continuous lesion. The term "continuous" in the context of a lesion is intended to mean a lesion that substantially blocks electrical conduction between tissue segments on opposite sides of the lesion.

The radiant energy emitter 140 is shown in FIG. 2 disposed within the balloon 126 located remotely from the target tissue (e.g., within a central lumen 116 of the catheter body 114 or otherwise disposed within the balloon). In one illustrated embodiment, the radiant energy transmitter (ablation element) 140 includes at least one optical fiber coupled to a distal light projecting, optical element, which cooperate to project a spot of ablative light energy through the instrument 100 to the target site 152 (in FIG. 6). The catheter body 114, projection balloon 126 and inflation/ablation fluids are all preferably substantially transparent to the radiant energy at the selected wavelength of the energy source to provide a low-loss transmission pathway from the radiant energy transmitter 140 to the target site 152. It should be understood that the term "balloon" encompasses deformable hollow shapes which can be inflated into various configurations including spherical, obloid, tear drop, etc., shapes dependent upon the requirements of the body cavity. Such balloon elements can be elastic or simply capable of unfolding or unwrapping into an expanded state. The balloon can further encompass multiple chamber configurations.

Also disposed within the instrument 100 is a visualization device, such as a reflectance sensor, preferably an endoscope 176 capable of capturing an image of the target site 152 and/or the instrument position. The endoscope 176 is typically an optical fiber bundle with a lens or other optical coupler at its distal end to receive light. The reflectance sensor/endoscope can also include an illumination source, such one or more optical fibers coupled to a light source or sources. Alternatively illumination and excitation light may be delivered though separate optical fibers as indicated by 128A in FIG. 2. Endoscopes are available commercially from various sources. The endoscope can further include an optical head assembly, as detailed in more detail below, to increase the field of view. In one illustrated embodiment, ablation element 140 and endoscope 176 are adapted for independent axial movement within the catheter body 14.

The term "endoscope" as used herein is intended to encompass optical imaging devices, generally, including but not limited to endoscopes, fiberscopes, cardioscopes, angioscopes and other optical fiber-based imaging devices. More generally, "endoscope" encompasses any light-guiding (or waveguide) structure capable of transmitting an "image" of an object to a location for viewing, such as display 14.

Preferably, spot lesions are formed at the target site 152 by applying radiant energy from the energy transmitter 140 to target tissue. The applied radiant energy may be applied in an energy range from about 50 Joules/cm$^2$ to about 1000 Joules/cm$^2$, or preferably from about 75 Joules/cm$^2$ to about 750 Joules/cm$^2$. The power levels applied by the energy emitter can range from about 10 Watts/cm$^2$ to about 150 Watts/cm$^2$ and the duration of energy delivery can range from about 1 second to about 1 minute, preferably from about 5 seconds to about 45 seconds, or more preferably from about 10 to about 30 seconds. For example, for power levels between 10 and 75 Watts/cm$^2$ it can be advantageous to apply the radiant energy for about 30 seconds. Lesser durations, e.g., of 10 to 20 seconds, can be used for power levels of 75 to 150 Watts/cm$^2$. In other words, the greater the power level, the lesser the residence time of the emitter at a specific location to achieve the desired ablation. It is to be understood the above figures are provided as examples and the energy, power and time duration figures set forth above are provided merely as examples and are not to be understood to be limited thereto.

In the illustrated embodiment of the ablation instrument 100 shown in FIGS. 5-6, the energy emitter 140 is a radiant energy emitter including at least one optical fiber coupled to a distal light projecting optical element, which cooperate to project a spot of ablative light energy through the instrument 100 to the target site 152. The optical element can further comprise one or more lens elements and/or refractive elements capable of projecting a spot or arc-shaped beam of radiation. Alternatively, the lesion generator may generate an annulus or partial ring of ablative radiation, as described in more detail in commonly owned U.S. Pat. No. 6,423,055 issued Jul. 22, 2002, herein incorporated by reference for its disclosure related thereto.

Automated Sweeping Motion for the Ablation Element

As described herein, the ablation element 140 not only moves axially within the balloon but also is configured to move in a rotational manner to allow a series of arc shaped energy emissions (which form arc shaped ablation segments) to be pieced together to form the completed lesion. The user may incrementally move, in a manual process, the ablation element 140 using a significant number of steps to complete the lesion when the ablation energy is emitted in an arc shaped pattern (so as to form an arc shaped ablation segment). In order to ensure a full complete lesion, the user typically at least partially overlaps a new arcuate lesion segment with a previously and immediately adjacent formed arcuate lesion segment to ensure completeness in the ablation process (i.e., no gaps in the lesion). However, as mentioned herein, this process can thus be time consuming since the user must carefully rotate the ablation element a selected number of degrees resulting in some overlap between the footprint (area) of the new ablation energy arc and the footprint of the previously formed lesion and then the ablation energy is applied.

The ablation energy is emitted for a predetermined period of time for each arcuate ablation segment that is formed. The amount of time can vary depending on a number of parameters including the size of the arcuate shaped segment being formed (e.g., the number of degrees for the arcuate shaped segment) and the degree of overlap with a previously formed arcuate shaped ablation segment and also can be based on anatomical considerations, such as the target location and the nature of the tissue landscape at the target location. For example, if the formed arcuate shaped segment has a footprint of 30 degrees, then the ablation energy may be emitted for a predetermined time period, such as 30 seconds to ensure proper ablation of the tissue. Typically, the larger the footprint of the ablated segment (i.e., the greater the number of degrees covered by the arcuate shaped ablation segment), the greater the amount of time needed to complete the tissue ablation.

In accordance with the present invention, the system includes optional functionality that allows for the ablation energy to undergo a programmed, controlled sweeping action resulting in an ablation being formed that occupies a greater surface area (larger footprint) than possible using a fixed, static energy emission. As described herein, the user can use a graphical user interface or the like to input the desired controlled parameters which are then executed and the ablation element 140 is moved in a controlled sweeping action over a predetermined number of degrees of travel. As described herein, the overall system has a number of safeguards to ensure proper ablation formation. For example, safety features, such as an emergency shut off, can be provided to allow the user to stop the ablation sweeping action at any time.

The sweeping action described herein that is provided by the automated ablation element of the present invention results in a larger arcuate shaped ablation segment being formed even though the actual ablation element is configured to emit a smaller sized arcuate shaped ablation segment as when the ablation element is held stationary.

Figure 12:
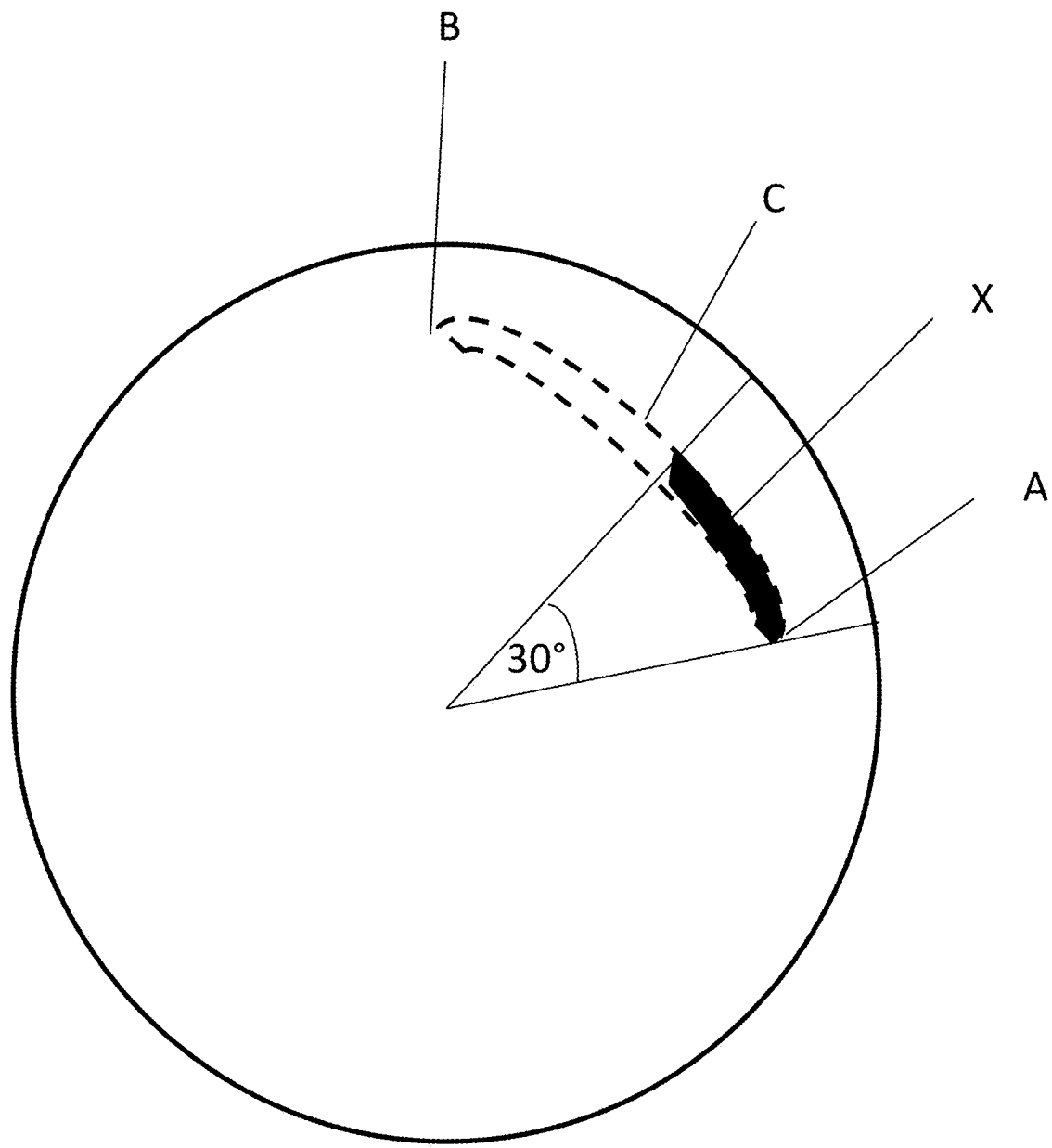
FIG. 12 illustrates the path of ablation at a treatment site using the sweeping action of the automated ablation element.

For example, FIG. 12 illustrates the path of ablation at a treatment site using the sweeping action of the automated ablation element 140. Like the embodiments discussed above, the automated ablation element 140 can be configured to emit an arcuate shaped ablation segment (X) of about 30 degrees (or another predetermined number of degrees) at any single location (as described herein, the angular measurement of the emitted energy is measured relative to the energy emitter and more specifically, the emitted energy has a prescribed subtended angle relative to the energy emitter. However, unlike the above embodiments, the sweeping action (caused by the controlled rotation of the ablation (energy) emitter) provided by the automated ablation element 140 allows it to move a predetermined number of degrees to one or both sides of the initial location of ablation in an arcuate path (sweeping motion) consistent with the initial ablation segment, thereby creating an arcuate shaped ablation segment greater than 30 degrees. In other words, the automated ablation element can be configured to sweep from the initial location of ablation (a first endpoint) to a second endpoint which is at the opposite end of the arcuate shaped ablation. In FIG. 12, while the initial arcuate shaped ablation segment X is at a first endpoint A, the sweeping action allows the automated ablation element to ablate from endpoint A to endpoint B in a sweeping motion, thereby creating a larger formed lesion segment. As described herein, one or more of the endpoints can be inputted by the user using a user interface, such as a touchscreen or other type of interface that allows the user to view the target ablation site and then mark the locations of the one or more endpoints. The coordinates of the one or more endpoints are then stored and in the case of the starting point, the ablation element is moved to the first stored coordinates (that identify and relate to the starting point) and the ablation process begins and in particular, the ablation element moves in a sweeping manner. In the case that the end point is also inputted by the user, the sweeping motion is designed so that the ablation element does not extend beyond the stored coordinates for the end point. This ensures that the formed arcuate shaped lesion is formed between the start point and the end point.

In at least one embodiment, the initial location of the automated ablation process can be the midpoint of the sweeping action for a given arcuate-shaped ablation segment. In other words, the automated ablation element can be configured to sweep left and right of the initial location of ablation (midpoint). For example, with reference to FIG. 12, the initial arcuate shaped ablation segment could begin at a midpoint C, and the automated ablation element could create a larger lesion segment by sweeping between endpoints A and B (as by rotating in a first direction toward point A and by rotating in a second direction toward point B). As such, with the automated ablation element, fewer lesion segments are needed to complete the continuous lesion and moreover, the process is more automated and requires less direct surgeon input and control over the energy emitter.

In one or more implementations, the automated ablation element 140 can be configured to sweep multiple times between endpoints of the ablation segment to complete the lesion segment. In at least one implementation, one "sweep" from one endpoint to the other endpoint of the segment is sufficient to complete the lesion segment.

Further, in the embodiments discussed above, ablative energy is directed to a single location to create a lesion segment, and once the lesion segment is created, the ablation element 140 is moved to a different (but overlapping) location, to create a second lesion segment. The movement of the ablation element to another location can be performed manually by the user or it can be part of an automated process in which based on the user's observation of the tissue at the target location and the quality and nature of the just ablated tissue (e.g., visual observations of the display of the user interface), the user can enter input commands to controllably move the ablation element to initiate the ablation process, such as a new sweeping action over a defined number of degrees. Once again, this new sweeping action can and typically does include some degree of overlap with the just previously formed lesion segment. The degree of overlap can be controlled and entered by the user as part of input control commands that control the operation (sweeping action) of the ablation element. Thus, if the ends of the arcuate shaped formed lesion include overlap from two discrete sweeping actions, the controller (related software) uses this information to calculate the degree of motion (including the residence time) of the ablation element in an intermediate region between the ends of the ablation segment.

As described herein and according to one implementation, the user begins by inputting a start point A and an endpoint B and then, the processor calculates the full path of the sweep to achieve a lesion extending between points A and B before energy delivery is initiated. The user then initiates energy delivery (via the energy emitter) and the sweeping of the energy emitter begins.

As described herein and according to another implementation, the user inputs a power level. The present system calculates an appropriate angular rate of sweep speed based on the power level. Then user then sets a start point of the sweep. Thus user initiates energy delivery (via the energy emitter) and the sweeping of the energy emitter. The user then terminates energy delivery and sweep once the desired end point is reached based on visual observation of the endoscopic image. This embodiment is thus thought of as being one in which the end point of the sweep is determined by the user "on the fly". In other words, the user set the start point but can stop the path of the sweep at any time based on information received from the visualization device or other obtained information.

This process of creating overlapping lesion segments is repeated until a continuous lesion is completed (formed). In the present embodiment for the automated ablation element, overlapping lesion segments are still formed; however, each formed lesion segment has a greater arc length due to the rotation (sweeping action) of the ablation element during ablation of the tissue. Thus, the continuous lesion can be created using fewer overlapping lesion segments as compared with the previous embodiment in which each arcuate shaped ablation segment is formed by emission of energy when the ablation element is fixed at one position. However, if the automated ablation element 140 uses the same amount of ablative energy (power) as the previous embodiment, the longer arcuate length lesion segments of the present embodiment would take longer to complete as the ablative energy is not directed to each location along the arc for as long a period of time (residence time) as compared with the stationary ablative element of the previous embodiment. As such, in one or more implementations, the power (energy) of the automated ablation element can be increased relative to the previous embodiment, such that a longer arcuate length lesion segment can be completed in a reduced amount of time. One of skill in the art will readily understand that the completeness and quality of the ablation depends largely on the level of power (energy) of the ablation element and the residence time of the ablation element over the target tissue (i.e., how long the ablation energy is emitted).

In further aspects of the automated ablation element embodiment, the overlap of the lesion segments can be minimal relative to the previous embodiment since the automated nature of the sweeping action of the ablation element allows for very precise control over the movement of the ablation element. As such, fewer lesion segments are needed to complete the continuous lesion. Further, in at least one embodiment, the automated ablation element can be configured to perform a real-time electrical assessment to confirm that a continuous lesion has been achieved. For example, the catheter can include electrodes that are configured to provide an electrical assessment of the sufficiency and quality of the formed lesion. As is known in the art, if the formed lesion includes any defect, such as a gap or break along its circumference, an electrical transmission will pass through such gap or break and can be detected.

Figure 13:
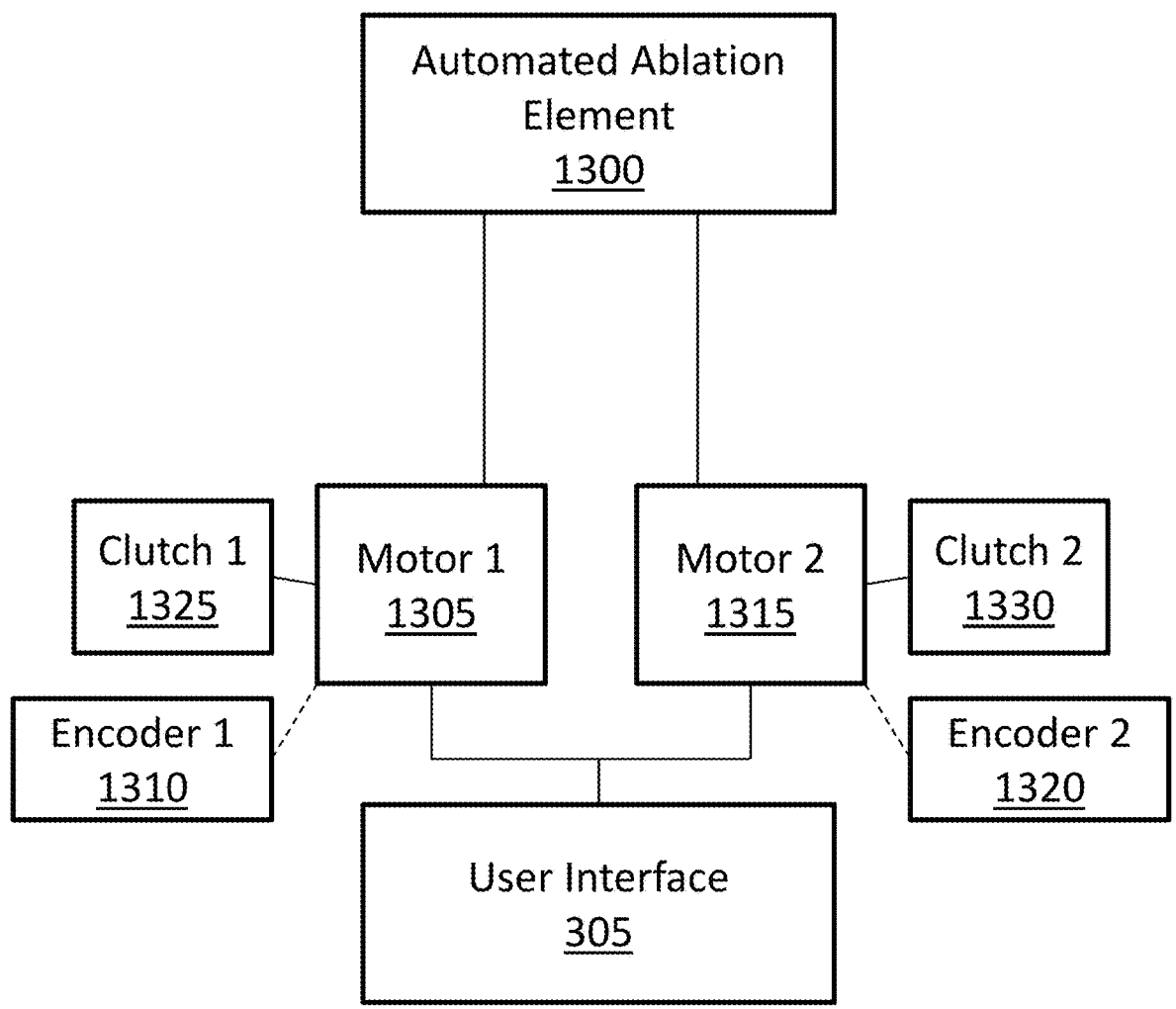
FIG. 13 is a block diagram of a computer system configured to control the motor of the automated ablation element.

The components of one exemplary automated ablation element 140, in accordance with at least one embodiment, are shown at FIG. 13. The automated ablation element 1300 can include a first motor 1305 configured to rotate the ablation element in a sweeping motion. In a preferred embodiment, the first motor 1305 is a servomotor, which allows for precise positioning, acceleration, and movement of the ablation element so as to achieve the desired sweeping motion thereof. The first motor 1305 can be coupled with a first encoder 1310, such as a rotary encoder. The first encoder 1310 is configured to provide position feedback and/or speed feedback to help control the motion and final position of the ablation element 1300. In one or more embodiments, the first motor 1305 can have a 1:1 gear ratio such that there is 1 motor rotation for every 1 rotation of the knob that is connected to a drive shaft for rotating the ablation element 1300.

It will be appreciated that the present ablation instrument can have other mechanical linkages for operatively connecting the first motor 1305 to the ablation element resulting in the controlled rotation of the ablation element in a sweeping manner (e.g., arcuate movement in a back and forth manner).

In at least one embodiment, the automated ablation element 1300 can include a second motor 1315 configured to move the ablation element axially within the catheter body and thus axially within the balloon. Accordingly, both the axial movement and rotation of the ablation element 1300 can be controlled in an automated manner as by mechanically linking the ablation element to one or more motors which control the movements of the ablation element. In certain embodiments, the second motor can also be coupled with a second encoder 1320 to control the axial movement of the ablation element.

It will be appreciated that the first and second motors 1305, 1315 can be operated successively or concurrently. When operated successively, the user first moves, in an automated manner, the energy emitter 140 either in the axial direction (which causes a change in the circumferential length of the formed lesion segment) or in a rotational direction, as described herein, and then performs the other operation. When used concurrently, the energy emitter moves axially and has a rotational movement component.

Figure 14:
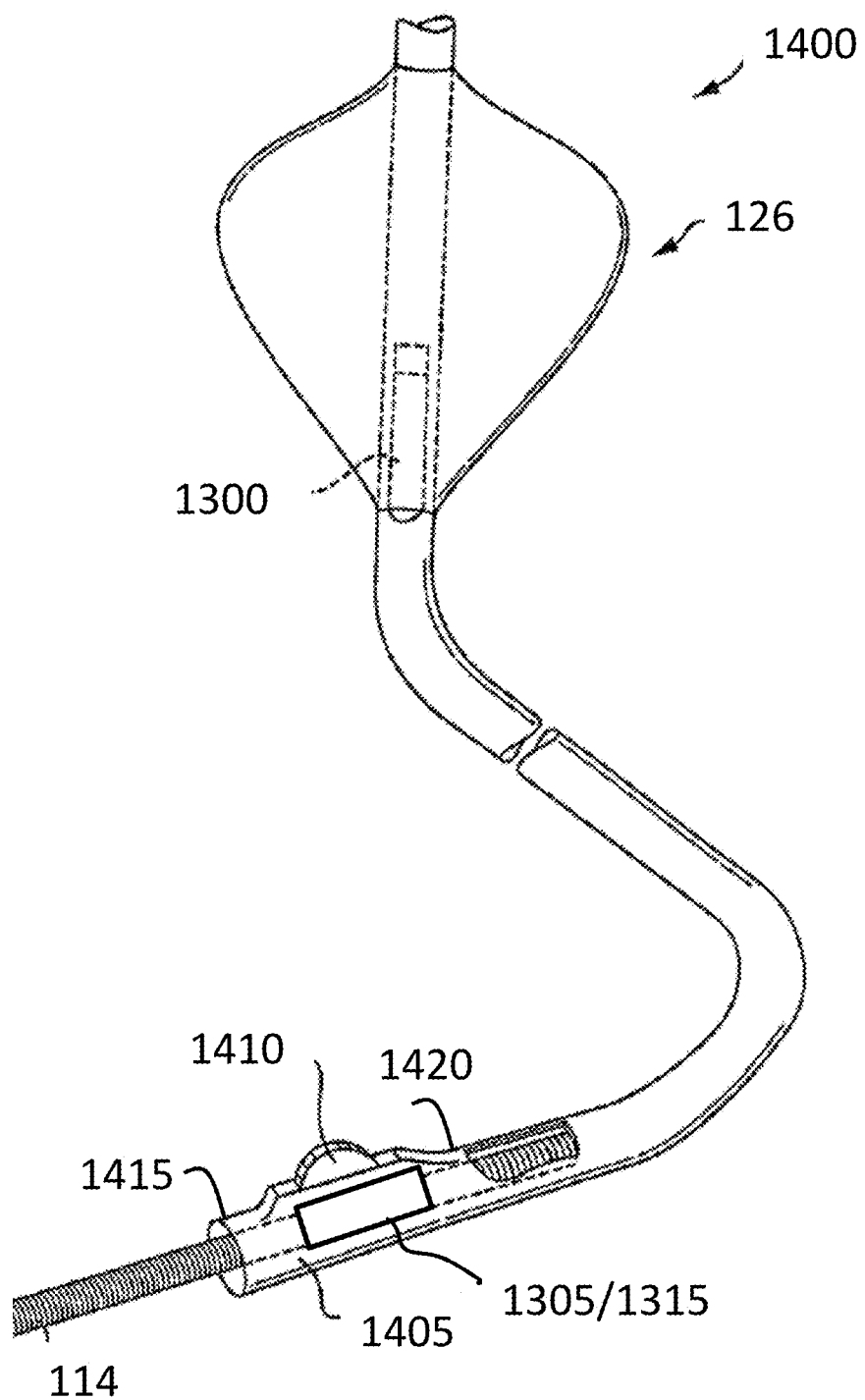
FIG. 14 is a schematic view of the cardiac ablation instrument comprising the automated ablation element, the ablation instrument further including a handle having one or more motors for controlling the movement of the automated ablation element.

The one or more motors 1305, 1315 can be located in any number of different locations. A schematic view of the cardiac ablation instrument 1400 comprising the automated ablation element 1300 including one or more motors is shown at FIG. 14. In FIG. 14, the one or more motors (1305/1315) can be located in a handle 1405 of the ablation instrument 1400. In particular, the handle 1405 can comprise an actuator 1410 for use by the operator to control the axial and/or rotational movement of the ablation element 1300 via motors 1305 and 1315. Further, the handle 1405 can be operably connected to a console at its proximal end 1415 and operably connected to the catheter (comprising the ablation element 1300) at its distal end 1420.

The console can comprise a display (display 14) and can be used to control the catheter and automated ablation element as discussed in further detail below. In implementations in which the one or more motors are located in the handle, the handle is re-sterilized following each procedure to ensure proper sanitary conditions.

Alternatively, the one or more motors (e.g., 1305/1315) can be located in the console of the instrument, or a separate unit that the handle is operatively connected to. In embodiments in which the motor(s) is located in the console or a separate unit, the motor can be connected to the ablation element via a drive shaft, which can be housed in a flexible cable. As such, in this embodiment, the motor does not need to be sterilized between uses as it will not be in contact with the patient. In this configuration, the drive shaft can be in the form of an elongated structure that is housed in the flexible cable and is operatively connected to the ablation element to cause rotation and/or axial movement thereof. The motor thus can be located remote from the catheter itself.

Referring again the FIG. 13, in one or more implementations, the ablation element 1300 can further include a first clutch 1325 and/or second clutch 1330. The one or more clutches (1325/1330) can be configured to disengage to avoid damage to the motor if the rotational or axial movement of the ablation element becomes jammed. Alternatively, the clutch (1325/1330) can be a slip-clutch, designed to slip when greater-than-normal resistance is encountered by the ablation element during rotational or axial movement. This mechanism thus protects the mechanical components of the device and prevents over internal damage due if unexpected resistance is encountered during controlled movement of the ablation element. In one or more embodiments, the pathway of the ablation for the automated ablation element can be predetermined by the operated using a graphical user interface (GUI) 305. In particular, using the GUI 305, the operator can input various parameters in order to program the pathway of the automated ablation element. The input parameters can include but are not limited to: the degree of the arc of ablation, the initial ablation location and end point(s) of the sweeping action, the power of the ablation energy for the particular ablation run, and the length of time for each sweeping motion. These parameters can be set and adjusted by the operator using the GUI 305. In at least one embodiment, software can be used to determine the pathway of the automated ablation element using certain parameters inputted by the operator, such as the initial ablation location and intermediate point, and the end point of the ablation. In this embodiment, the software (e.g. based on an algorithm), rather than the operator, can calculate the pathway of the ablation, including the degree of the arc and the power of the ablation energy, based on a few input parameters. In one or more embodiments, the input parameters can be modified by the operator before and during the process of creating a continuous lesion via ablation.

The operator can input parameters using the GUI 305 via various methods such as an input joystick or a touchscreen operatively connected to the console of the instrument. The operator can view the input parameters for the ablation element on the display of the console. Once the pathway is determined (either by the operator or by the software), the ablation instrument can be configured to perform a test run in which the ablation element is axially moved within the catheter to the desired location and rotated at the desired location, but no ablative energy is used. More specifically, the motor (via input using the GUI) can configure the automated ablation element to rotate the ablation element back and forth in a sweeping motion at the location of ablation, but without ablating the tissue. Instead, only an aiming light (beam) attached to the ablation instrument (as described in further detail below) is activated. As such, this test run can be used to confirm the pathway of the ablation using the aiming beam prior to ablating the tissue. Once the test run has confirmed the pathway, the ablation instrument can be configured to perform the ablation.

The ablation instrument can optionally feature a manual override device (e.g., knob) allowing the operator to manually control the rotational and/or axial movement of the automated ablation element. In one or more embodiments, the manual override device (knob) can be located on the console. In certain embodiments, the operator can manually override the input parameters to alter the positioning and/or pathway of ablation element. In at least one embodiment, the motor can also have an override feature to maintain the ablation power and pathway if the manual knob (that controls manual movement of the ablation element) is moved accidently during ablation.

Figure 15:
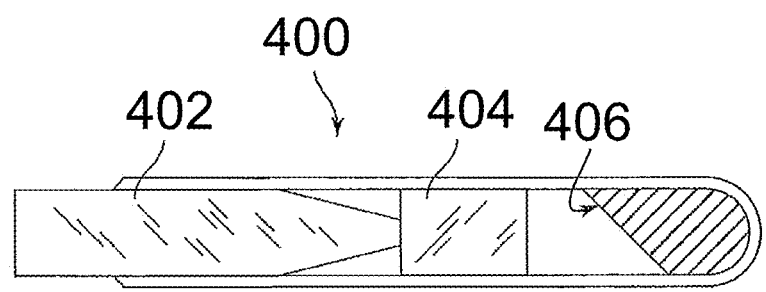
FIG. 15 is a cross-sectional view of one exemplary ablation element.

In one or more implementations, as illustrated in FIG. 15, an automated ablation element can comprise an optical fiber, such as a chiseled-end optical fiber, a graduated refractive index (GRIN) lens and a reflector. More particularly, FIG. 15 is a schematic cross-sectional illustration of one embodiment of a radiant energy emitter 400 according to the invention. In one embodiment, the radiant energy is electromagnetic radiation, e.g., coherent or laser light, and the energy emitter 400 projects a beam of radiation that forms a spot or arc-shaped exposure pattern upon impingement with a target surface. For example, radiant energy emitter 400 can include an optical fiber 402, the distal end of which can be beveled into an energy-emitting face of reduced cross-section. The fiber 402 passes a beam of light to a gradient index (GRIN) lens 404, which serves to collimate the beam, keeping the beam width substantially the same, over the projected distance. The beam that exits the GRIN lens 404 is reflected by reflector 406 in an angular direction from about 5 degrees to about 110 degrees relative to from the light's path along the longitudinal axis of the catheter. Generally, the angle of reflection from the central axis of the optical fiber 402 can range from about 30 to nearly 90 degrees. In other words, the angle of projection, from the optical axis of the fiber 402 (or lens 404) will be between about 5 to 60 degrees forward of perpendicular. The reflector 406 can be in the form of a total internal reflecting (TIR) mirror element; however, other types of suitable reflectors can be equally used. Suitable automated ablation elements are disclosed in U.S. Pat. No. 8,696,653, which is hereby incorporated by reference in its entirety.

In one or more implementations, the automated ablation element can further comprise a foot pedal to allow for control over one or more operations of the catheter. For example, a foot pedal can be used to apply power to the ablation element and also can be used to control the operation of one or more of the motors described above.

Aiming Light

Since the radiant energy (e.g., a laser) emitted from the energy emitter 140 is typically outside the visual light spectrum that can be detected by the human eye, the ablation instrument 100 includes an aiming light preferably having a pulsed operating mode in which visible light from the aiming light unit is delivered in pulses to cause intermittent illumination of the tissue at the target site 152. This gives the aiming light an appearance of being a blinking light. By delivering the visible aiming light in pulses, the electrophysiologist is able to directly observe the tissue while it is being treated at the target site 152, using an endoscope, between the aiming light pulses.

During an ablation procedure, the endoscope 176 is used to determine the extent of tissue ablation by sensing the change in appearance of the tissue as it is ablated and at a time when the aiming beam is in an off cycle via the display 14. In other words, between the blinking (pulses) of the aiming light, the electrophysiologist can observe the treated tissue to determine how the treatment is progressing since the endoscope 176 is used to determine the extent of tissue ablation by sensing the change in appearance of the tissue as it is ablated and at a time when the aiming beam is in an off cycle. However, many conditions may cause the actual detection of change in appearance of the tissue being ablated to be difficult and/or unreliable in regards to whether proper spot lesions are formed by the energy transmitter 140 on the tissue at the ablation treatment site 152. For instance, insufficient illumination at the treatment site 152 can make it difficult, if not impossible, to ascertain whether proper spot lesions were formed at the treatment site as viewed on display 14.

As also described herein, the endoscope 176 is also used to sense a change in the degree of movement or perturbation in the distal pulmonary vein blood pool).

Figure 7:
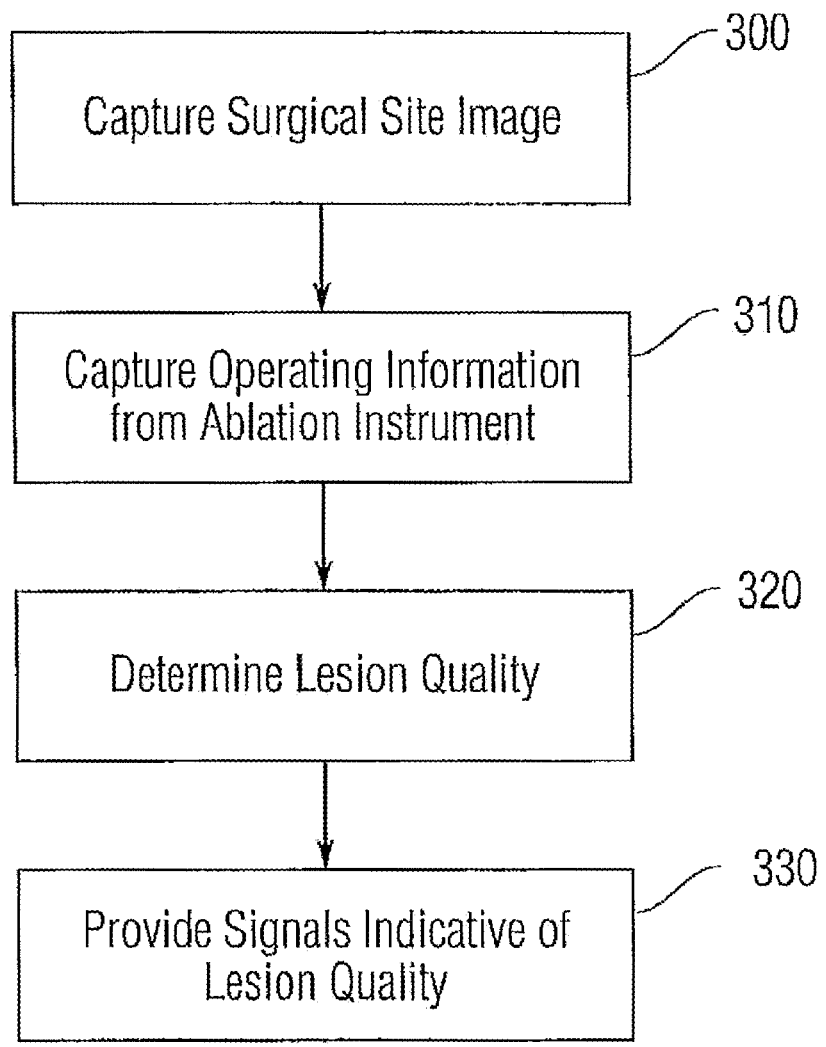
FIG. 7 is a flow diagram illustrating the steps performed by the ablation system of FIG. 1 for determining the quality of lesions formed during treatment that entails an intracardiac ablation procedure.

The processor 12 of ablator system 10 obviates this problem by determining the quality of the lesion formed on the tissue at the target site 152 which may be viewed on monitor 14 and/or indicated to an electrophysiologist via visual overlay or audio cues. With reference now to the flow diagram of FIG. 7, the method of operation for determining the quality of spot lesions at an ablation treatment site 152 will now be discussed.

Starting at step 300, the processor 12 captures the image from endoscope 176 of the tissue being ablated at the treatment site. At step 310, the processor 12 also captures information relating to the energy transmitter 140 from controller 16. The captured energy transmitter 140 information includes: the amount of radiant energy (power) applied by energy transmitter 140 on the tissue at the treatment site 152 to form spot lesions; the distance the energy transmitter 140 is from tissue to be ablated via spot lesions; and the rate of movement of energy transmitter 140 relative to the tissue at the treatment site 152. It is to be appreciated that aforesaid information captured regarding energy transmitter 140 is not to be understood to be limited thereto as more or less information may be captured that is necessary to determine the quality of the spot lesions formed on the tissue at the treatment site and/or visually determine the completion of the procedure by observation of a change in the characteristics of the blood pool in the pulmonary vein.

The processor 12 then preferably uses algorithmic techniques to determine whether a sufficient spot lesion has just recently been formed on the tissue at the treatment site (step 320). In other words, given the distance the energy transmitter 140 is located from the tissue at the treatment site 152, the rate of movement of the energy transmitter 140 relative to the tissue at the treatment site 152 (e.g., the amount of time that energy is applied to the tissue at a given location), and the amount of energy being applied, a determination is made as to whether a sufficient spot lesion has been formed on the tissue at a location which the energy transmitter is applying ablation energy thereto. A lookup table or other similar means may also be used by processor 12 for determining the aforesaid lesion quality. A spot lesion is to be understood as being sufficient when it comprises enough scar tissue effective to block the transmission of electrical signals therethrough.

The processor 12 is preferably further operative and configured to provide a signal to the electrophysiologist indicative of whether a sufficient spot lesion has been formed (step 330). This indicative signal may be provided in the event an insufficient or no spot lesion was formed on the tissue at the treatment site 152 that was subject to the energy transmitter 140 dispersing energy thereto. This indicative signal may be an audio and/or visual signal. The audio signal may consist of a warning tone and the visual signal may consist of a marker (e.g., color red) superimposed on the display 14 illustrating the treatment site 152 (provided via endoscope 176) at the location at which the insufficient spot lesion was determined. Thus, when image processor 12 determines an insufficient spot lesion has been formed, the aforesaid warning signal is promptly provided to the electrophysiologist enabling the electrophysiologist to revisit the tissue having the insufficient lesion and make proper adjustments with the energy transmitter 140 (e.g., apply more energy, close the distance between energy transmitter 140 and the treatment site and/or slow the movement of energy transmitter 140 relative to the treatment site) so as to now form sufficient lesions.

Figure 9:
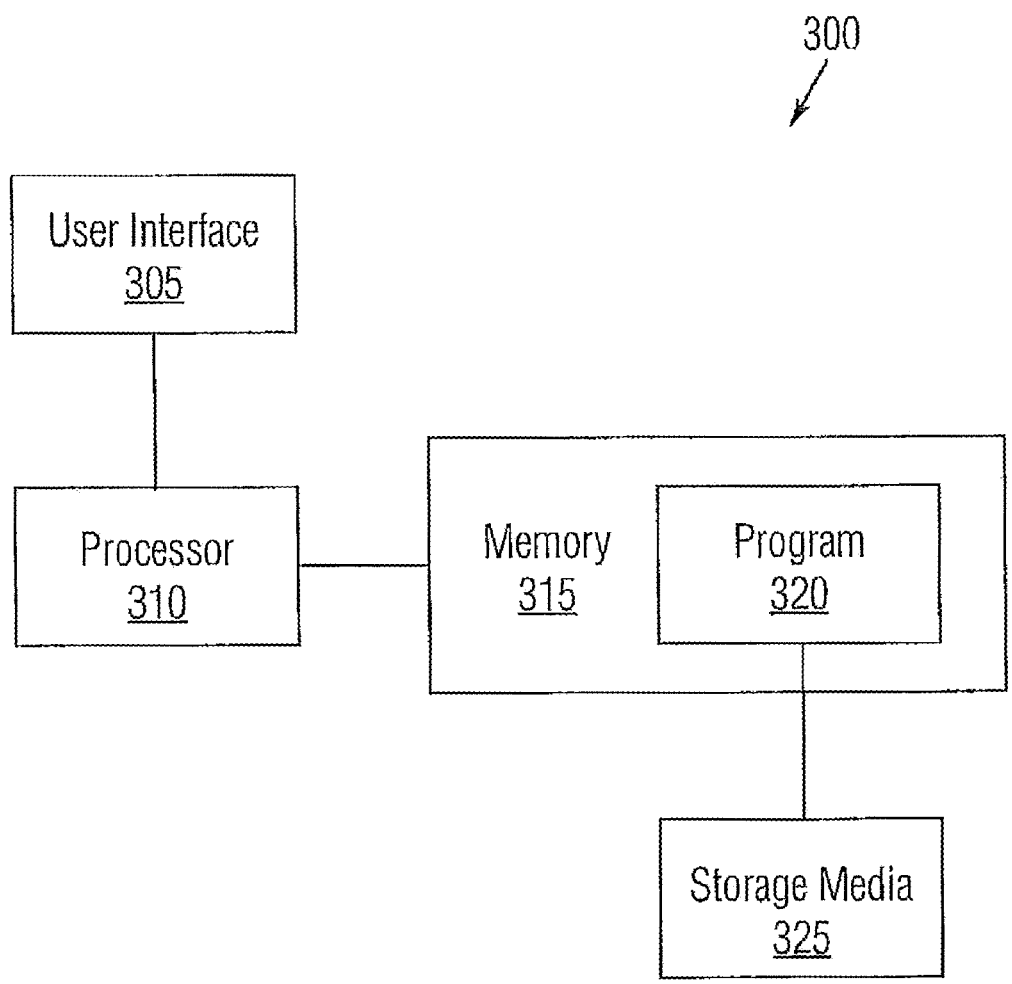
FIG. 9 is a block diagram of a computer system configured to employ one ablation method of the present invention.

FIG. 9 is a block diagram of one computer system 300 configured for employment of method 100. System 300 includes a user interface 305, a processor 310, and a memory 315. System 300 may be implemented on a general purpose microcomputer, such as one of the members of the Sun® Microsystems family of computer systems, one of the members of the IBM® Personal Computer family, one of the members of the Apple® Computer family, or a myriad other conventional workstations. Although system 300 is represented herein as a standalone system, it is not limited to such, but instead can be coupled to other computer systems via a network (not shown).

Memory 315 is a memory for storing data and instructions suitable for controlling the operation of processor 310. An implementation of memory 315 would include a random access memory (RAM), a hard drive and a read only memory (ROM). One of the components stored in memory 315 is a program 320.

Program 320 includes instructions for controlling processor 310 to execute method 100. Program 320 may be implemented as a single module or as a plurality of modules that operate in cooperation with one another. Program 320 is contemplated as representing a software embodiment of the method described hereinabove.

User interface 305 includes an input device, such as a keyboard, touch screen, tablet, or speech recognition subsystem, for enabling a user to communicate information and command selections to processor 310. User interface 305 also includes an output device such as a display or a printer. In the case of a touch screen, the input and output functions are provided by the same structure. A cursor control such as a mouse, track-ball, or joy stick, allows the user to manipulate a cursor on the display for communicating additional information and command selections to processor 310.

While program 320 is indicated as already loaded into memory 315, it may be configured on a storage media 325 for subsequent loading into memory 315. Storage media 325 can be any conventional storage media such as a magnetic tape, an optical storage media, a compact disc, or a floppy disc. Alternatively, storage media 325 can be a random access memory, or other type of electronic storage, located on a remote storage system.

The methods described herein have been indicated in connection with flow diagrams that facilitate a description of the principal processes; however, certain blocks can be invoked in an arbitrary order, such as when the events drive the program flow such as in an object-oriented program. Accordingly, the flow diagram is to be understood as an example flow and that the blocks can be invoked in a different order than as illustrated.

It should be understood that various combination, alternatives and modifications of the present invention could be devised by those skilled in the art. The present invention is intended to embrace all such alternatives, modifications and variances that fall within the scope of the appended claims.

Although described in connection with cardiac ablation procedures, it should be clear that the instruments and systems of the present invention can be used for a variety of other procedures where treatment with radiant energy is desirable, including laparoscopic, endoluminal, perivisceral, endoscopic, thoracoscopic, intra-articular and hybrid approaches.

Thus, the instrument 100 is merely exemplary of one type of ablation device that can be used in combination with the endoscope/imaging device of the present invention.

Figure 10:
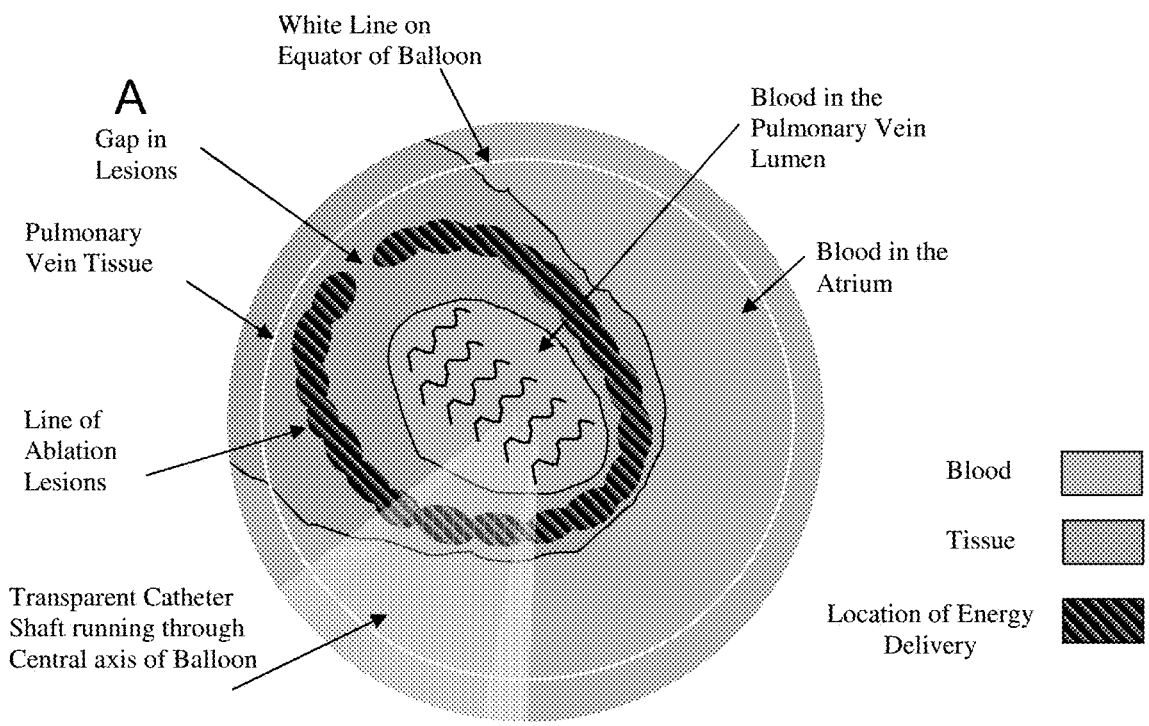
FIG. 10 is a representative view of a treatment site, prior to beginning the ablation procedure, from along a longitudinal axis of a catheter.

Visual Confirmation of Target Tissue (e.g., a Pulmonary Vein) Isolation by Monitoring Blood Pool Characteristics FIG. 10 is a representative endoscopic view of a treatment site from along a longitudinal axis of the catheter. This view is preferably displayed on a display, such as a monitor and the ablated tissue can be displayed in a visually distinguished manner relative to the de-novo (untreated) tissue.

Figure 11:
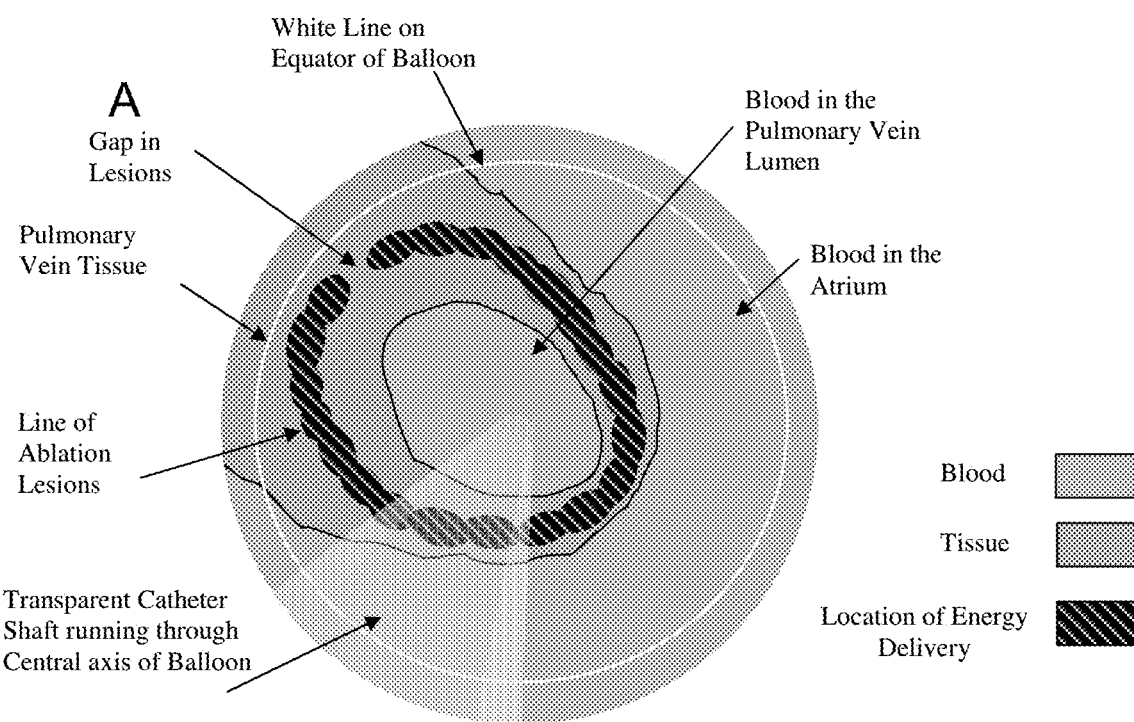
FIG. 11 is a representative view of a treatment site, after completion of the ablation procedure, from along a longitudinal axis of a catheter.

In FIGS. 10 and 11, the areas of blood/tissue are visually differentiated from the locations of the energy delivery (the formation of the lesions) by the use of cross-hatching. The catheter shaft and balloon are also visually distinguished from the blood/tissue and the lesions (by cross-hatching). As discussed herein, in FIGS. 10 and 11, the cross-hatched areas denote blood/tissue.

The principles of the present invention are readily appreciated in view of FIG. 10 and FIG. 11 in which FIG. 10 shows the treatment site prior to beginning the ablation procedure, while FIG. 11 shows the treatment site after completion of the ablation procedure and after a complete ablation is formed. As will be apparent from viewing FIGS. 10 and 11, the blood pool in FIG. 10 is shown as having increased perturbation as a result of contraction of the muscles at the target site. For example, the target site can be the pulmonary vein and thus, the contraction of muscles around the pulmonary vein causes such perturbation in the distal blood pool. Visually, the blood pool will have the appearance similar to a rough ocean in that there is high degree of waves and other local disturbances particularly evident at the borders between blood and tissue. Conversely and after the pulmonary vein has been effectively isolated as a result of a complete continuous lesion (ablation) being formed around the pulmonary vein, the distal blood pool (i.e., the blood in the pulmonary vein) has a much reduced visible pattern of perturbation (due to a reduction in electrical activity/electrical isolation at the target site). Visually, the blood pool will have a more placid appearance compared to the initial appearance (which is more vigorous and choppy, etc.). Thus, as described herein, a comparison between the initial image (which serves as a baseline) and a real-time image is indicative and can be used to determine, in real-time, if the ablation is complete (i.e., if the lesion was formed successively so as to isolate the target tissue, which in this case is around pulmonary vein).

The Imaging System

The imaging system in accordance with the present invention includes an appropriate imaging device that is configured to monitor, in real time, the condition of the tissue at the treatment site and in particular, allow the physician to readily distinguish between ablated tissue and de novo tissue that has not been ablated. The imaging system also further allows the physician to monitor, in real-time, the conditions of the distal blood pool (e.g., blood within the pulmonary vein) prior to beginning the procedure, during the procedure and after the procedure is complete. The imaging system allows the observed image to be displayed in real-time on a display and/or recorded and stored in memory.

An endoscope (as discussed previously) can be used to obtain an image of the ablated tissue as described herein. The endoscope is inserted into the body of the catheter and positioned adjacent the area of interest to allow viewing in real-time of the area.

It will be appreciated that the imaging system of the present invention is not limited to the use of an endoscope but instead, any number of different types of imaging systems can be used so long as they provide a real-time image of the treatment site that can be observed on the display.

Image Analysis (Software)

The software of the present invention can be configured such that the visual patterns of the distal blood pool can be analyzed. As discussed herein, contraction of the muscles at the target site is caused by electrical conduction across the tissue and this normal muscle traction will cause the distal blood pool (e.g., the blood in the pulmonary vein) to have increased perturbation. Increased perturbation can be observed visually in that the blood will have certain characteristics that are indicative of blood motion or perturbation. For example, highly perturbed blood will have a set of visual characteristics/patterns such as an increased appearance of waves and other local distortions/disturbances that are visible especially at the blood/tissue border. The blood will not have a smooth, flat uniform appearance when the muscles are contracting at the target site. Thus, the baseline image that is preferably stored in memory before the procedure begins will show the visual condition of the blood pool when it is subjected to muscle contraction.

As the ablation procedure begins and the lesion series (ablation) is formed at the target site, decreased electrical activity occurs due to the lesion formation causing progressive electrical isolation of the target (e.g., the objective can be to electrically isolate the pulmonary vein). The decreased electrical activity is a result of less muscle contraction at the target site and therefore, the characteristics of the distal blood pool will likewise change. For example, there will be a progressive lessening in the degree of perturbation (degree of local disturbances) of the distal blood pool. In other words, as the ablation procedure continues, the distal blood pool increasingly has more of a placid visual appearance due to a lessening in the perturbation characteristics (local disturbances) that are present in the baseline image.

The software can also be configured such that a degree of turbulence in the distal blood pool or the actual displacement of the blood/tissue border can be classified using a scoring system which includes analyzing the degree of correlation between the visual image of the distal blood pool prior to beginning the ablation procedure (i.e., the baseline image) and the real-time image of the distal blood pool. More specifically, the software has a processor that compares the real-time image to the baseline image and determines the degree of correlation. An algorithm can be used to calculate the degree of correlation between the real-time image and the baseline image and it is desirable in such comparison that the degree of correlation is low. In other words, it is desirable that the real-time image not have the visual characteristics of the baseline image since it is desirable that the distal blood pool have a placid appearance or close thereto after a complete lesion is formed.

Alternatively, the processor can be configured to compare the real-time image with an optimal image that represents a placid blood pool (i.e., an ideal condition indicative of complete electrical isolation of the target tissue (e.g., pulmonary vein)). In this embodiment, it is desirable to have a high degree of correlation between the real-time image and the optimal image since the optimal image represents perfect electrical isolation of the target. In yet another embodiment, the processor can use both the initial pre-procedure image and the optimal image to calculate the quality of the ablation and more particularly, calculate the level of isolation of the target tissue. The software and method of the present invention thus provides for visual confirmation of pulmonary vein isolation during the ablation procedure.

It will also be appreciated that the processor can be used to compare or contrast more characteristics that are indicative of blood perturbation in order to assess the degree of electrical isolation of the target tissue. By comparing the one or more characteristics, the processor can be configured to calculate the degree of completeness of the ablation by analyzing the real-time image relative to the baseline image.

It will also be appreciated that the baseline image can be visually distinguished from the real-time image by use of different colors for each of the images. For example, the baseline image can be displayed with a first color of the display (e.g., monitor) and the real-time image can be displayed with a second color that is visually distinguishable relative to the first color. Thus, when the two images are superimposed (e.g., the real-time image overlies the baseline), the differences in the level of perturbation of the distal blood pool can be visually detected. For example, the baseline image, in the first color, is represented by visual indicia (such as wave lines), while the real-time image is represented by much less visual indicia (such as wave lines) in the second color or alternatively, a smooth placid blood pool will be represented by a lack of indicia that represents perturbation (i.e., a lack of wave lines). Thus, the lack of indicia, in the second color, is indicative that the ablation is complete and the target site (e.g., the pulmonary vein) has been electrically isolated. Image registration software can then be used to combine the two images in proper alignment.

The type of visualization is especially important in intraoperational use where it is desirable for the physician to understand the quality of the formed ablation and whether the main objective of electrically isolating the target tissue has been achieved.

In accordance with the present invention, one technique for detecting a significant change in the movement of the distal blood pool border comprises measuring the excursion of the border of the blood pool and involves the following steps: (a) provide a signal gated to either a high voltage recurring component of the ECG or at the point of photographic evidence of the maximum excursion of the blood pool border throughout the cardiac cycle; (b) measure the length of two or more orthogonal diagonals at the time of activation gated to either of these signals; (c) compute a first maximum, minimum, and average length measurement; (d) measure the length of two or more orthogonal diagonals at a recurring isoelectric ECG phase in between gated activation or at the point of photographic evidence of the minimum excursion of the blood pool border throughout the cardiac cycle; (e) compute a second maximum, minimum and average length measurement; (f) calculate a difference between the first and second measurements; (g) provide a means to program an indicator representing an achievement of a predetermined percentage reduction in the excursion of the border of the blood pool measurements or at a point potentially referencing a representative point at which electrical activity has been shown to have been eliminated.

Review of Ablation Quality

The present invention thus allows the electrophysiologist to view the formed ablation(s) (lesion) in real-time and to evaluate the quality of the formed ablation(s) to allow the electrophysiologist to decide whether additional ablation treatment is needed. For example, if the electrophysiologist views the display and receives feedback that the target tissue (pulmonary vein) has not been electrically isolated as a result of the formed ablation(s) including a defect, such as a void (gap or break) along its length, or is otherwise not acceptable, then the electrophysiologist can continue the procedure and correct the deficiencies in the ablation.

A gap formed along the length of the lesion will prevent the distal blood pool from assuming the desired, lessened perturbation condition and thus, once the electrophysiologist reevaluates and locates the gap or other deficiency, the electrophysiologist can correct such deficiency. After such correction, the electrophysiologist can compare the real-time image which will allow visual confirmation of the desired isolation of the target tissue (pulmonary vein) as represented by the reduced perturbation (placid) condition of the distal blood pool.

The feedback presented to the electrophysiologist can also include other qualitative information such as a calculated degree of change in the perturbation of the distal blood pool and other information that can be displayed at the same time that the real-time image of the target site is displayed. It will be appreciated that the electrophysiologist uses all of the information provided to him/her, including the information concerning the degree of perturbation of the distal blood pool and other visual information concerning the quality/sufficiency of the ablation (i.e., visual information that indicated a gap or break in the ablation (lesion)). The user can then use other means for assessing the location of the gap(s) in the lesion to allow for corrective action to be taken.

U.S. patent application publication No. 2009/0326320 discloses other details of exemplary imaging systems that can be implemented, at least in part, and is hereby incorporated by reference in its entirety. It will be understood that one or more of the features disclosed in that document can be implemented in the imaging system of the present invention in that the imaging system can include more than one means for visualizing the treatment site and providing the user (electrophysiologist) with helpful feedback and information concerning the quality of the lesion (i.e., whether the lesion is a continuous, uninterrupted structure, etc.).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for forming an arcuate shaped lesion at a target tissue location using an ablation instrument that has an energy emitter that is configured to move in a sweeping motion to form the arcuate shaped lesion in target tissue at the target tissue location comprising the steps of:

inputting a preselected power level of the energy emitter;
selecting a start point of the energy emitter to begin the sweeping motion;
initiating energy delivery and commencing the sweeping motion of the energy emitter beginning at the start point and under operation of a first motor; and terminating the energy delivery and sweep once a desired end point is reached based on visual observation of an image of the arcuate shaped lesion formed in the target tissue that is obtained in real time with a visualization device;

wherein the ablation instrument includes a manual override knob that allows manual control over rotational and axial movement of the energy emitter and the motor has an override mode that maintains delivery of energy from the energy emitter and maintains the sweeping motion of the energy emitter even if the manual override knob is moved.

2. The method of claim 1, wherein the step of commencing the sweeping motion comprises operating the first motor that is operatively coupled to the energy emitter and is configured to rotate the energy emitter in the sweeping motion, wherein energy is delivered during the entire sweeping motion of the energy emitter.

3. The method of claim 2, further including operating a second motor to cause axial movement of the energy emitter.

4. The method of claim 1, wherein the visualization device comprises an endoscope.

5. The method of claim 1, further including a step of inputting a degree of an arc of ablation energy emitted by the energy emitter to form a discrete lesion segment that in combination with one or more additional discrete lesion segments form the arcuate shaped lesion and wherein a processor calculates an angular rate of sweep speed based on the inputted degree of the arc of the energy emitter.

6. The method of claim 1, wherein a processor calculates a residence time of the energy emitter that is defined as a total time in which the energy emitter moves along an arcuate path to form a discrete lesion segment that forms part of the arcuate shaped lesion.

* * * * *